US012636266B2

(12) United States Patent
Gibbs et al.

(10) Patent No.: US 12,636,266 B2
(45) Date of Patent: May 26, 2026

(54) INDANE-, INDENE-, AZAINDANE-, AND AZAINDENE-AMINES AS ACTIVATORS OF SEROTONIN RECEPTORS

(71) Applicant: Rivo Bio, Inc., Boston, MA (US)

(72) Inventors: Alan C. Gibbs, Wyndmoor, PA (US); Rebecca Aron, Brookline, MA (US)

(73) Assignee: Rivo Bio, Inc., Boston, MA (US)

( * ) Notice: Subject to any disclaimer, the term of this patent is extended or adjusted under 35 U.S.C. 154(b) by 0 days.

(21) Appl. No.: 19/027,091

(22) Filed: Jan. 17, 2025

(65) Prior Publication Data

US 2025/0228798 A1 Jul. 17, 2025

Related U.S. Application Data

(60) Provisional application No. 63/621,764, filed on Jan. 17, 2024.

(51) Int. Cl.

| | |
|---|---|
| *A61K 31/137* | (2006.01) |
| *A61K 31/397* | (2006.01) |
| *A61K 31/435* | (2006.01) |
| *A61P 25/24* | (2006.01) |
| *C07C 211/30* | (2006.01) |
| *C07D 205/04* | (2006.01) |
| *C07D 333/78* | (2006.01) |
| *C07D 401/08* | (2006.01) |
| *C07D 405/10* | (2006.01) |

(52) U.S. Cl.

CPC .......... *A61K 31/137* (2013.01); *A61K 31/397* (2013.01); *A61K 31/435* (2013.01); *A61P 25/24* (2018.01); *C07C 211/30* (2013.01); *C07D 205/04* (2013.01); *C07D 333/78* (2013.01); *C07D 401/08* (2013.01); *C07D 405/10* (2013.01)

(58) Field of Classification Search

None

See application file for complete search history.

(56) References Cited

U.S. PATENT DOCUMENTS

| | | | |
|---|---|---|---|
| 6,388,090 | B2 | 5/2002 | Huhtala et al. |
| 2010/0029707 | A1 | 2/2010 | Uchikawa et al. |

FOREIGN PATENT DOCUMENTS

| | | | |
|---|---|---|---|
| CN | 102924410 | A | 2/2013 |
| CN | 103396387 | A | 11/2013 |
| WO | 9608466 | A1 | 3/1996 |
| WO | 97905098 | A1 | 2/1997 |
| WO | 9963977 | A2 | 12/1999 |
| WO | 2007148808 | A1 | 12/2007 |
| WO | 2008062468 | A2 | 5/2008 |
| WO | 2012112964 | A2 | 8/2012 |
| WO | 2018026371 | A1 | 2/2018 |
| WO | 2023250268 | A1 | 12/2023 |

OTHER PUBLICATIONS

Anderson (Chem and Biol 10:787-797, 2003) (Year: 2003).*

Thiel (Nature Biotechnol 2:513-519, 2004) (Year: 2004).*

CAS RN 2103322-51-4 (entered into STN on Jul. 26, 2017) (Year: 2017).*

CAS RN 2241944-24-9 (entered into STN on Aug. 30, 2018) (Year: 2018).*

CAS RN 2416050-84-3 (entered into STN on May 7, 2020) (Year: 2020).*

Fukatsu et al., "Synthesis of a Novel Series of Benzocycloalkene Derivatives as Melatonin Receptor Agonists," J. Med. Chem., 2002, 45, Mar. 12, 2002, 10 pages.

Hoashi et al., "Discovery of a Potent and Orally Bioavailable Melatonin Receptor Agonist," Journal of Medicinal Chemistry, J. Med. Chem., 2021, Mar. 26, 2025, 16 pages.

Kolyadina et al., "Geometric isomers of 9-picolylideneazafluorenes," Jan. 1, 1993, 2 pages.

Mander et al., "Chemical constituents of Galbulimima species. VI. Structure of hamandridine," Australian Journal of Chemistry, 2 pages.

Search Report received in International Application No. PCT/US2025/011981 dated Apr. 10, 2025, 9 pages.

Written Opinion received in International Application No. PCT/US2025/011981 dated Apr. 10, 2025, 8 pages.

* cited by examiner

*Primary Examiner* — Craig D Ricci

(74) *Attorney, Agent, or Firm* — Jeff B. Vockrodt; CM Law

(57) ABSTRACT

The present invention relates to novel chemical compounds of indane-, indene-, azaindane-, and azaindene-amines that act as 5-HT2A receptor agonists. These compounds are designed to offer improved therapeutic profiles for the treatment of a variety of neuropsychiatric, neurological, and neurodegenerative disorders. Also disclosed are methods for the synthesis and pharmaceutical use of these compounds.

19 Claims, No Drawings

INDANE-, INDENE-, AZAINDANE-, AND AZAINDENE-AMINES AS ACTIVATORS OF SEROTONIN RECEPTORS

BACKGROUND

The 5-HT2A receptor is a serotonin receptor subtype known to play a crucial role in various central nervous system processes. The 5-HT2A receptor plays a pivotal role in modulating neurotransmission, cognitive processes, and emotion, among other effects. The 5-HT2A receptor signaling network is implicated in the pathophysiology and therefore therapeutic effects for a range of neuropsychiatric conditions, including depression, schizophrenia, and anxiety disorders, as well as in certain neurological and neurodegenerative diseases. Currently available treatments for these disorders are limited by suboptimal efficacy, adverse side effects, and the development of treatment resistance.

5-HT2A agonists such as N,N-dimethyltryptamine, psilocybin, LSD, and various other hallucinogenic or non-hallucinogenic analogs are psychoactive compounds of interest for modulating neural activity towards the treatment of several neuropsychiatric, neurological, and neurodegenerative disorders.

There is a continuous need for novel therapeutic agents that can offer improved efficacy, safety profiles, and reduced side effects.

SUMMARY

In an aspect, the present disclosure relates to novel chemical compounds of indane-, indene-, azaindane-, and azaindene-amines that act as 5-HT2A receptor agonists. These compounds are designed to offer improved therapeutic profiles for the treatment of a variety of neuropsychiatric, neurological, and neurodegenerative disorders. In an aspect, the present disclosure provides methods for the synthesis and pharmaceutical use of these compounds.

In one embodiment, the present disclosure provides a compound having the formula of Formula (Ia):

(Ia)

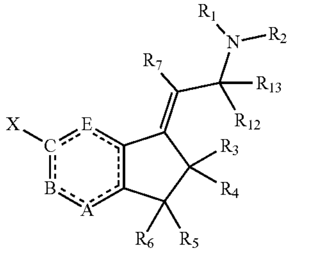

wherein:

- $R_1$ and $R_2$ are independently a H, D, $C_1$-$C_6$ alkyl, $R_1$ and $R_2$ are independently substituted or unsubstituted heteroalkyl, heteroaryl, aryl, or alkyl; or $R_1$ and $R_2$ can be taken together to form a 3-10 membered substituted or unsubstituted ring;
- $R_3$, $R_4$, and $R_5$ are independently a H, D, halogen, $CF_3$, or a $C_1$-$C_6$ alkyl, heteroalkyl, aryl, or heteroaryl;
- $R_3$ and $R_5$ can optionally be taken together to form a 4-10 membered substituted or unsubstituted ring;
- $R_6$ is H or D;
- A, B, and E are independently a N, CH, CD, $C_1$-$C_6$ alkyl, halogen, $CF_3$, COH, $COR_8$, $OR_8$, $OC(O)R_8$, or $NR_8C(O)R_8$;
- A or E is optionally taken to be an S while B is omitted resulting in a 5 membered thiophene ring;
- C is a C or N;
- A and B can optionally be taken together to form a 4-10 membered substituted or unsubstituted ring;
- $R_7$ is a H, D, halogen, or $C_1$-$C_6$ alkyl;
- $R_8$ is a H, D, $CF_3$ or a C1-$C_6$ alkyl, aryl, or heteroaryl;
- X is a H, D, halogen, OH, $OR_{11}$, $SO_2$, $NH_2$, $NR_{11}$, CN, $COOR_{11}$, $COR_{11}$, $CONR_{11}$, $NCOR_{11}$, a substituted or unsubstituted heteroalkyl, aryl, heteroaryl, $C_1$-$C_6$ alkyl, or absent;
- X and E can optionally be taken together to form a 4-10 membered substituted or unsubstituted ring;
- $R_{11}$ is a $C_1$-$C_6$ alkyl, substituted or unsubstituted heteroaryl, heteroalkyl, aryl, or alkyl; and
- $R_{12}$ and $R_{13}$ are independently a H, D, $C_1$-$C_6$ alkyl, halogen, heteroalkyl, $CF_3$, OH, or where $R_{12}$ can be taken together with $R_1$ to form a 3-10 membered substituted or unsubstituted ring;

a pharmaceutically acceptable salt thereof, wherein one or more of the following is present;

- X is F, OH, or $OR_{11}$;
- E is COH or $COR_8$;
- X and E form a 4-10 membered substituted or unsubstituted ring;
- C or E is N; or
- $R_2$ is isopropyl.

The dashed line in the formula (Ia) signifies the optional presence of a bond in the case where a double bond may be present.

In an embodiment, the present disclosure provides a compound, a pharmaceutically acceptable salt thereof, of Formula (Ib):

(Ib)

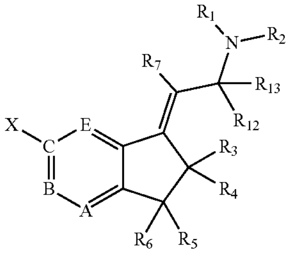

In an embodiment, the present disclosure provides a compound, a pharmaceutically acceptable salt thereof, of Formula (Ic):

(Ic)

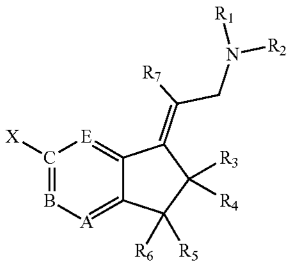

wherein:

$R_1$ and $R_2$ are independently a H, D, $C_1$-$C_6$ alkyl, or where $R_1$ and $R_2$ can be taken together to form a 3-10 membered substituted or unsubstituted ring;

$R_3$, $R_4$, and $R_5$ are independently a H, D, halogen, $CF_3$, or a $C_1$-$C_6$ alkyl, heteroalkyl, aryl, or heteroaryl;

$R_3$ and $R_5$ can optionally be taken together to form a 4-10 membered substituted or unsubstituted ring;

$R_6$ is H or D;

A, B, and E are independently a N, CH, CD, $C_1$-$C_6$ alkyl, halogen, $CF_3$, COH, $COR_8$, $OR_8$, $OC(O)R_8$, or $NR_8C(O)R_8$;

A or E is optionally taken to be an S while B is omitted resulting in a 5 membered thiophene ring;

C is a C or N;

$R_7$ is a H, D, halogen, or $C_1$-$C_6$ alkyl;

$R_8$ is a H, D, $CF_3$ or a $C_1$-$C_6$ alkyl, aryl, or heteroaryl;

X is a H, D, halogen, OH, $OR_{11}$, or absent;

X and E can optionally be taken together to form a 4-10 membered substituted or unsubstituted ring; and $R_{11}$ is a $C_1$-$C_6$ alkyl;

wherein one or more of the following is present;

X is F, OH, or $OR_{11}$;

E is COH or $COR_8$;

X and E form a 4-10 membered substituted or unsubstituted ring;

C or E is N; or $R_2$ is isopropyl.

In an embodiment, the compound may be a compound of Formula (IIIa):

Formula (IIIa)

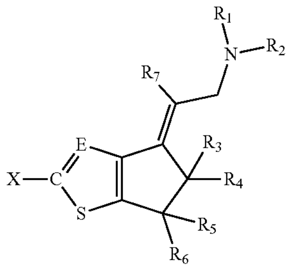

wherein C is a carbon atom, and other substituents are as described above.

In an embodiment, the compound may be a compound of Formula (IIIb):

Formula (IIIb)

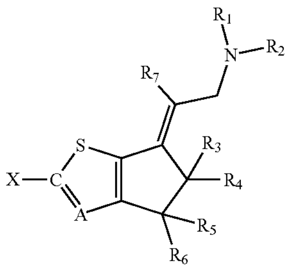

wherein C is a carbon atom, and other substituents are as described above.

In an embodiment, the compound may be a compound of Formula (II):

Formula (II)

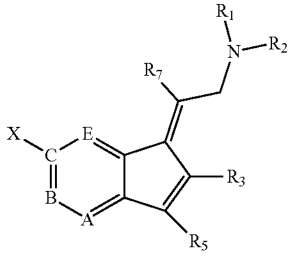

wherein C is a carbon atom, and other substituents are as described above.

In an embodiment, the compound may be a compound of Formula (IVa):

Formula (IVa)

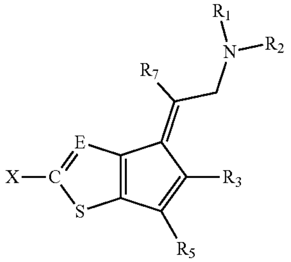

wherein C is a carbon atom, and other substituents are as described above.

In an embodiment, the compound may be a compound of Formula (IVb):

Formula (IVb)

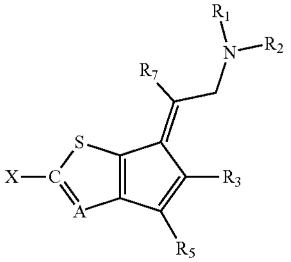

wherein C is a carbon atom, and other substituents are as described above.

In an embodiment, the compound may be selected from:

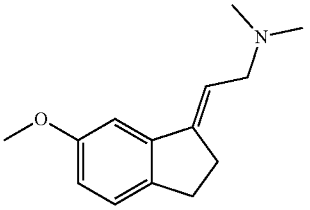

,

-continued

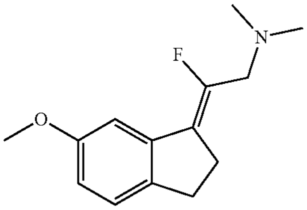

,

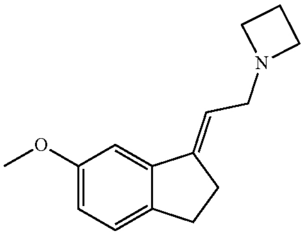

,

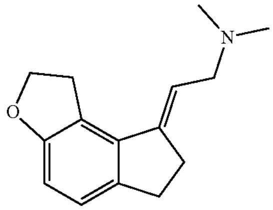

,

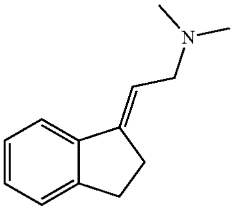

,

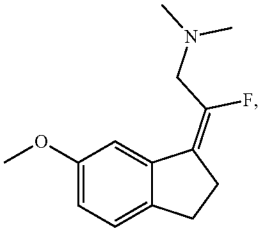

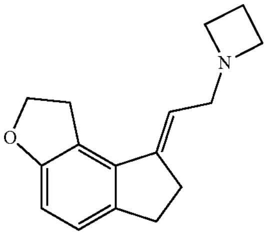

,

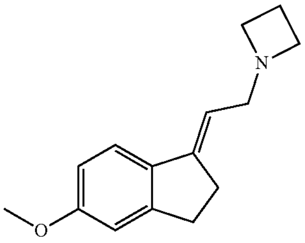

,

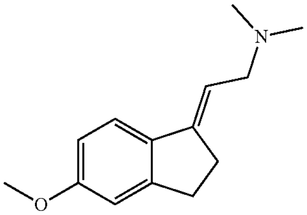

,

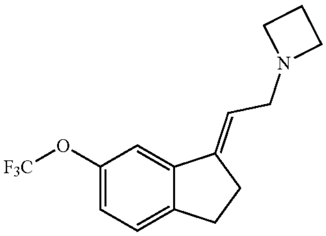

,

-continued

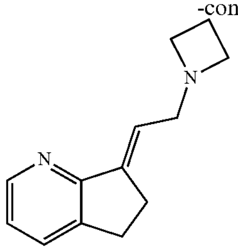

,

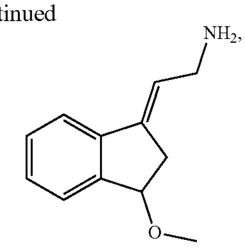

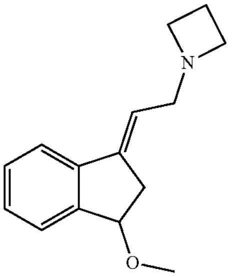

,

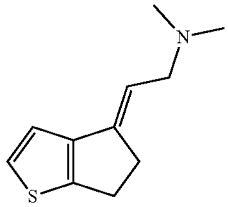

,

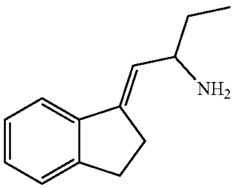

, or

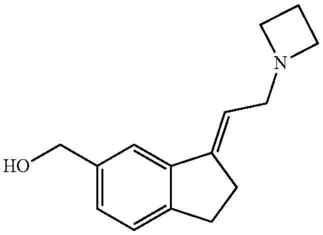

.

In some embodiments, $R_1$ and $R_2$ are $CH_3$. In some embodiments, X is a F, OH, or $OR_{11}$. In some embodiments, $R_7$ is F or H. In some embodiments, $R_3$ is $CH_3$. In some embodiments, E is COH or $COR_8$. In some embodiments, E is $COCH_3$. In some embodiments, X and E form a 4-10 membered substituted or unsubstituted ring. In some embodiments, C or E is N. In some embodiments, $R_2$ is isopropyl. In some embodiments, $R_1$ and $R_2$ form a 3-10 membered substituted or unsubstituted ring.

In some embodiments, the compound acts as an agonist of a 5-HT2A receptor. In some embodiments, the compound has over a 90% (5-HT) activity at 5-HT2A.

In one embodiment, the compound of Formula (I) or Formula (II) is combined with a pharmaceutical carrier.

In one embodiment, the compound of Formula (I) or Formula (II) is used to treat a neuropsychiatric, neurological, and neurodegenerative disorder. In some embodiments, the treatment is for depression, schizophrenia, or anxiety disorders.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications, and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The singular form "a", "an" and "the" include plural references unless the context clearly dictates otherwise. For example, the term "a pharmaceutically acceptable carrier" may include a plurality of pharmaceutically acceptable carriers, including mixtures thereof.

The term "carrier" refers to a diluent, adjuvant, excipient, or vehicle with which the therapeutic is administered and includes, but is not limited to, such liquids and powders that are hydrophilic substances, hydrophobic substances and substances that possess both hydrophilic and hydrophobic properties such as emulsifiers.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

The term "pharmaceutically acceptable" as used herein, refers to a component of a pharmaceutical composition that is compatible with the other ingredients of the formulation and not overly deleterious to the recipient thereof.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

A person having ordinary skill in the art will appreciate that "D", in the case of, for example, "CD" refers to deuterium, and will appreciate that this refers to levels of deuterium at the specific position that is isotopically enriched relative to the level of isotope found in nature. These are typically referred to as deuterated compounds.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroalkyl" refers to a stable saturated or unsaturated 3- to 20-membered ring which consists of two to nineteen carbon atoms and from one to six heteroatoms selected from the group consisting of nitrogen, oxygen and sulfur, and which is attached to the rest of the molecule by a single bond.

The term "substituted" used herein means any of the groups described herein (e.g., alkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

The term "neurological disease or condition" as used herein, means a disease or condition selected from: a neuropsychiatric disorder, such as depression (including severe depression such as treatment-resistant depression, major depressive disorder and persistent depressive disorder), catatonic depression, a depressive disorder due to a medical condition, postpartum depression, premenstrual dysphoric disorder, or seasonal affective disorder, anxiety, anxiety disorder, social anxiety disorder, general anxiety disorder (GAD), avolition disorder, bipolar disorder (including bipolar I disorder and bipolar II disorder), post-traumatic stress disorder, body dysmorphic disorder, abnormalities of mood or emotion, including the above conditions, dysthymia, schizoaffective disorder, schizophrenia and other psychotic disorders, panic disorder, traumatic stress disorders, phobic disorders, and personality disorders with abnormal mood, such as borderline personality disorder, schizoid and schizotypal disorders and suicide ideation, or rumination/unproductive repetitive thoughts negatively impacting one's behavior/mood/ability to focus, obsessive-compulsive disorder, addiction (including substance use disorder such as addiction to nicotine, alcohol, cocaine, opioids, amphetamine, methamphetamine, heroin, morphine, phencyclidine, 3,4-methylenedioxy-methamphetamine, as well as other addictive substances), addictive behavior (including eating, gambling, sex, pornography, videogames, work, exercise, spiritual obsession, self-harm, travel and shopping addiction), eating disorder (including anorexia nervosa, bulimia nervosa and binge eating disorder), and pain (including pain associated with migraine or headache or chronic pain).

The terms "administer," "administering" or "administration" as used herein refer to administering a compound or pharmaceutically acceptable salt of the compound or a composition or formulation comprising the compound or pharmaceutically acceptable salt of the compound to a patient.

The term "in need of treatment" and the term "in need thereof" when referring to treatment are used interchangeably and refer to a judgment made by a caregiver (e.g. physician, nurse, nurse practitioner) that a patient will benefit from treatment.

The terms "treat" and "treatment" refer herein to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented. "Treatment" can, when concerning depression, also include reducing at least one sign or symptom of depression. Examples of a sign or symptom of depression include depressed mood, diminished interest in activities, weight loss or gain, decrease or increase in appetite, insomnia or hypersomnia, psychomotor agitation or retardation, fatigue or loss of energy, feelings of worthlessness or excessive or inappropriate guilt, diminished ability to concentrate or indecisiveness, or suicidal ideation or behavior.

The term "effective amount" or "therapeutically effective amount" as used herein, refers to the amount of active agent that elicits the biological or medicinal response in a tissue, system, or individual that is being sought by a researcher, healthcare provider or individual.

Compounds

The present disclosure in one aspect involves compounds that are agonists of 5-HT2A receptors. In some embodiments, the compounds of Formula (I) or Formula (II) comprise the compounds of Table 1.

TABLE 1

| Compound Number | Structure |
|---|---|
| 5 | 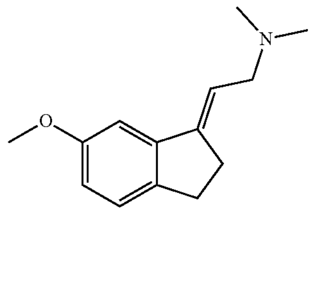 |

TABLE 1-continued
| Compound Number | Structure |
| --- | --- |
| 6 | 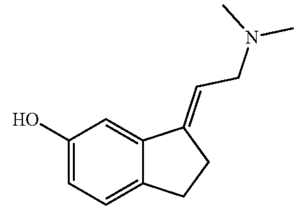 |
| 7 | 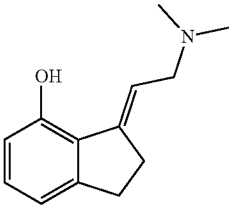 |
| 8 | 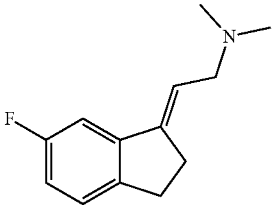 |
| 9 | 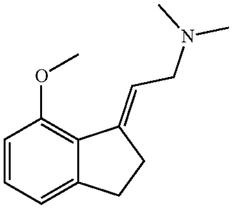 [SMILES: COc1cccc2c1/C(=C/CN(C)C)CC2] |
| 10 | 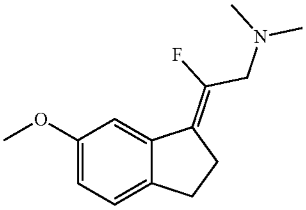 |
| 11 | 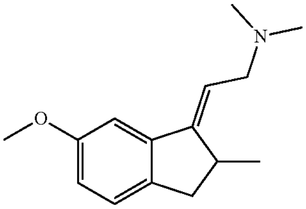 |
| 12 | 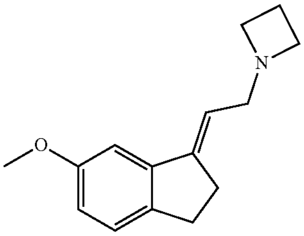 [SMILES: COc1ccc2c(c1)/C(=C/CN1CCC1)CC2] |
TABLE 1-continued
| Compound Number | Structure |
| --- | --- |
| 13 | 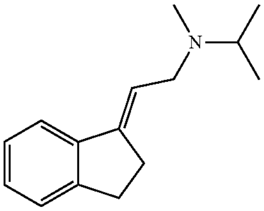 [SMILES: CC(C)N(C)C/C=C1\CCc2ccccc21] |
| 14 | 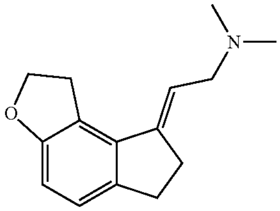 [SMILES: CN(C)C/C=C1\CCc2ccc3c(c21)CCO3] |
| 15 | 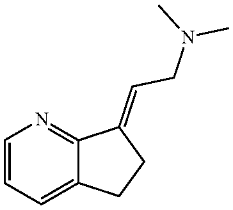 |
| 16 | 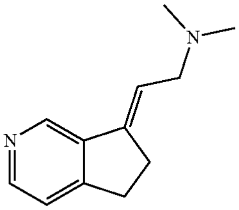 |
| 17 | 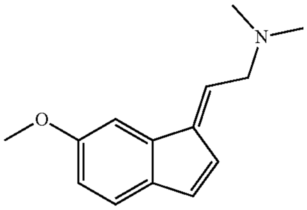 |
| 18 | 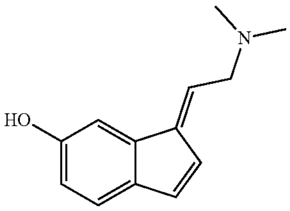 |
| 19 | 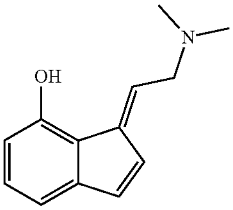 |

TABLE 1-continued
| Compound Number | Structure |
|---|---|
| 20 | 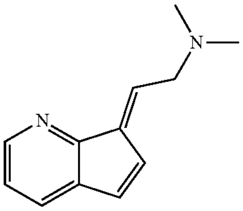 |
| 21 | 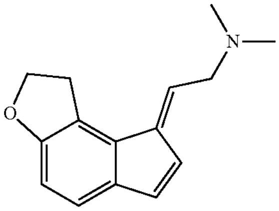 [SMILES: CN(C)C/C=C1\C=Cc2ccc3c(c21)CCO3] |
| 22 | 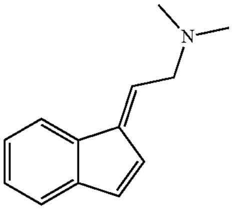 |
| 23 | 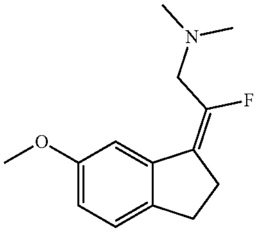 Z |
| 24 | 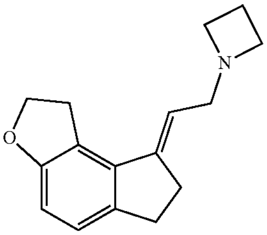 [SMILES: C(/CN1CCC1)=C1/CCc2ccc3c(c21)CCO3] |
| 25 | 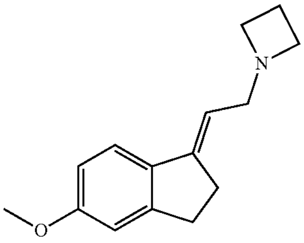 [SMILES: COc1ccc2c(c1)CC/C2=C\CN1CCC1] |
| 26 | 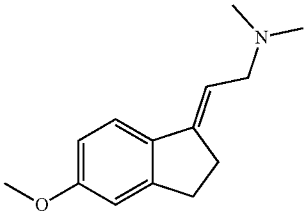 |
| 27 | 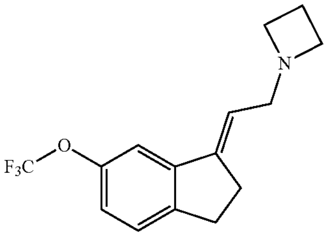 [SMILES: FC(F)(F)Oc1ccc2c(c1)/C(=C/CN1CCC1)CC2] |
| 28 | 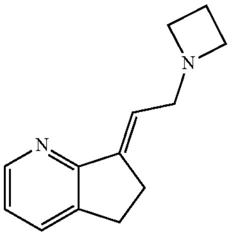 [SMILES: C(/CN1CCC1)=C1/CCc2cccnc21] |
| 29 | 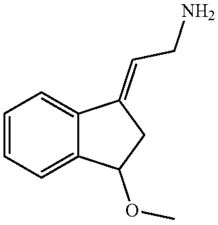 |
| 30 | 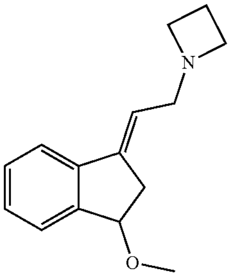 [SMILES: COC1C/C(=C\CN2CCC2)c2ccccc21] |
| 31 | 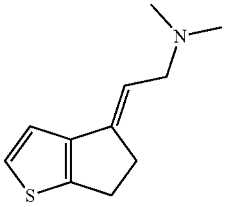 |

TABLE 1-continued
| Compound Number | Structure |
|---|---|
| 32 | 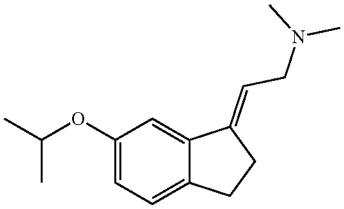 [SMILES: CC(C)Oc1ccc2c(c1)/C(=C/CN(C)C)CC2] |
| 33 | 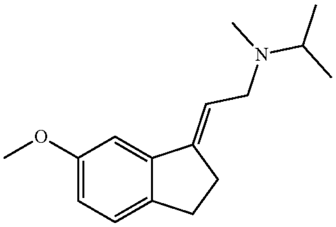 [SMILES: COc1ccc2c(c1)/C(=C/CN(C)C(C)C)CC2] |
| 34 | 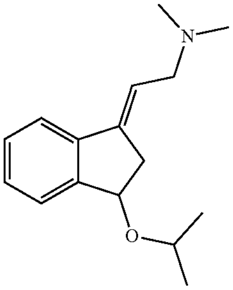 [SMILES: CC(C)OC1C/C(=C\CN(C)C)c2ccccc21] |
| 35 | 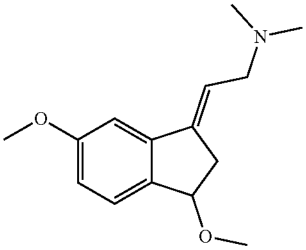 |
| 36 | 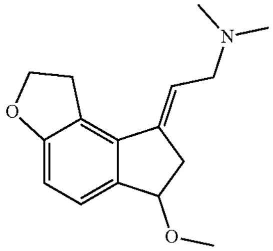 [SMILES: COC1C/C(=C\CN(C)C)c2c1ccc1c2CCO1] |
| 37 | 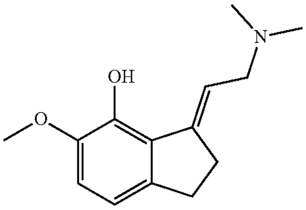 |
TABLE 1-continued
| Compound Number | Structure |
|---|---|
| 38 | 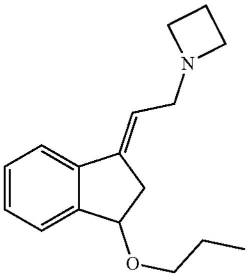 [SMILES: CCCOC1C/C(=C\CN2CCC2)c2ccccc21] |
| 39 | 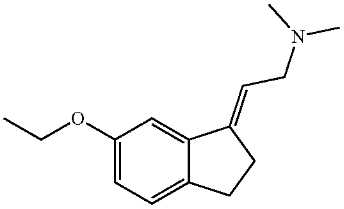 [SMILES: CCOc1ccc2c(c1)/C(=C/CN(C)C)CC2] |
| 40 | 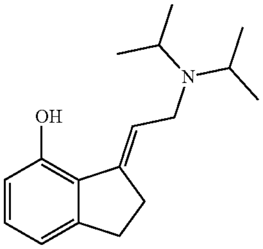 [SMILES: CC(C)N(C/C=C1\CCc2cccc(O)c21)C(C)C] |
| 41 | 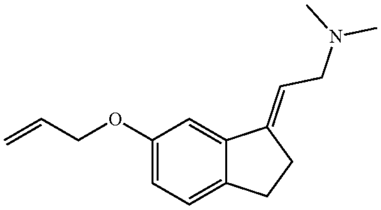 [SMILES: C=CCOc1ccc2c(c1)/C(=C/CN(C)C)CC2] |
| 42 | 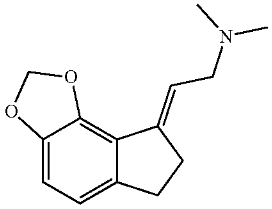 [SMILES: CN(C)C/C=C1\CCc2ccc3c(c21)OCO3] |
| 43 | 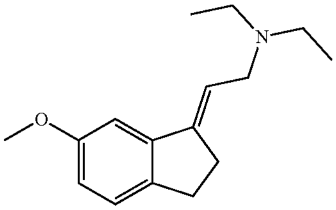 [SMILES: CCN(CC)C/C=C1\CCc2ccc(OC)cc21] |

TABLE 1-continued
| Compound Number | Structure |
|---|---|
| 44 | 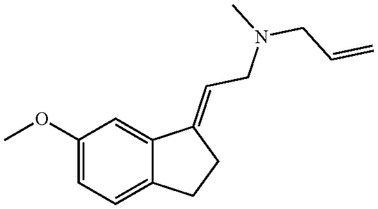 [SMILES: C=CCN(C)C/C=C1\CCc2ccc(OC)cc21] |
| 45 | 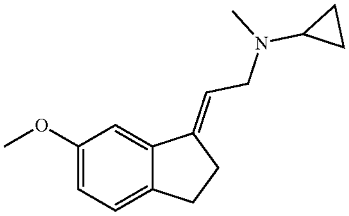 [SMILES: COc1ccc2c(c1)/C(=C/CN(C)C1CC1)CC2] |
| 46 | 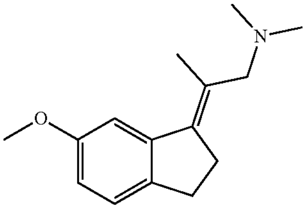 |
| 47 | 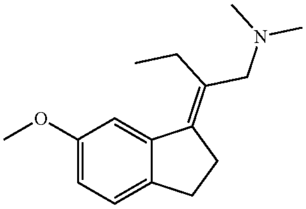 |
| 48 | 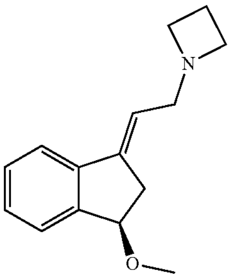 [SMILES: CO[C@@H]1C/C(=C\CN2CCC2)c2ccccc21] |
| 49 | 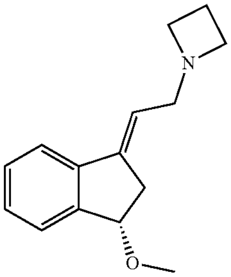 [SMILES: CO[C@H]1C/C(=C\CN2CCC2)c2ccccc21] |
TABLE 1-continued
| Compound Number | Structure |
|---|---|
| 50 | 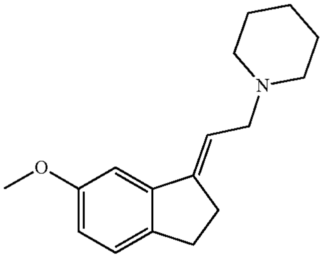 [SMILES: COc1ccc2c(c1)/C(=C/CN1CCCCC1)CC2] |
| 51 | 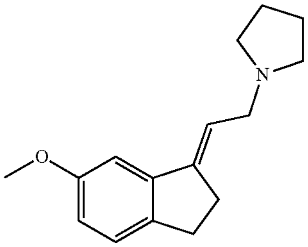 [SMILES: COc1ccc2c(c1)/C(=C/CN1CCCC1)CC2] |
| 52 | 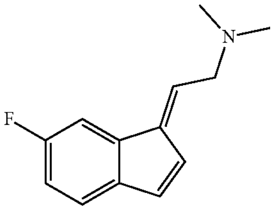 |
| 53 | 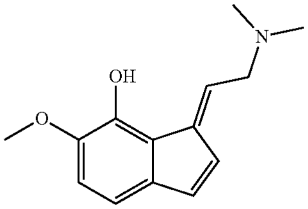 |
| 54 | 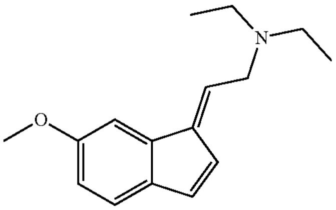 [SMILES: CCN(CC)C/C=C1\C=Cc2ccc(OC)cc21] |
| 55 | 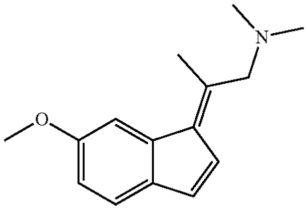 |

TABLE 1-continued
| Compound Number | Structure |
|---|---|
| 56 | 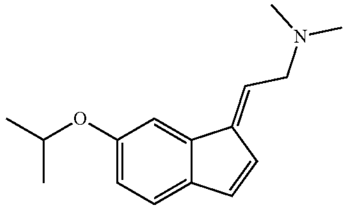 [SMILES: CC(C)Oc1ccc2c(c1)/C(=C/CN(C)C)C=C2] |
| 57 | 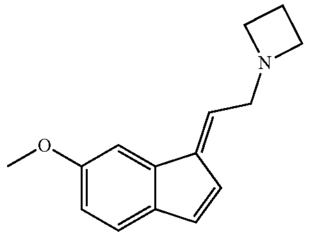 [SMILES: COc1ccc2c(c1)/C(=C/CN1CCC1)C=C2] |
| 58 | 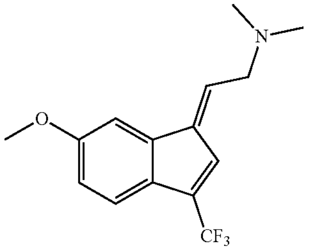 |
| 59 | 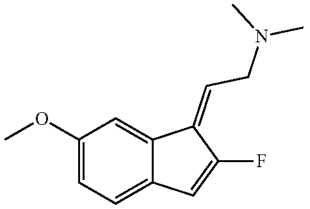 |
| 60 | 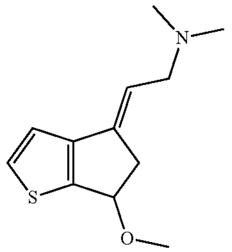 |
| 61 | 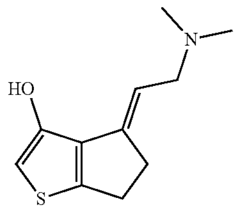 |
TABLE 1-continued
| Compound Number | Structure |
|---|---|
| 62 | 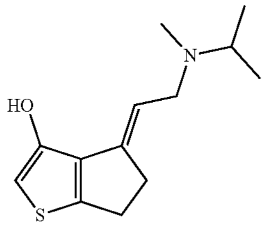 [SMILES: CC(C)N(C)C/C=C1\CCc2scc(O)c21] |
| 63 | 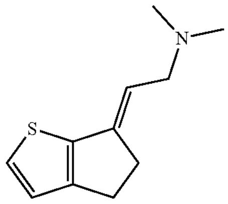 |
| 64 | 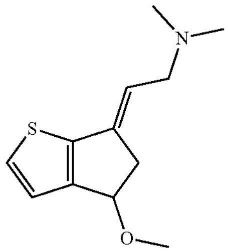 |
| 65 | 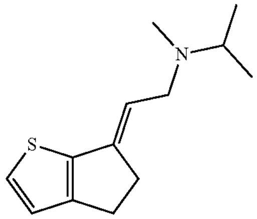 |
| 66 | 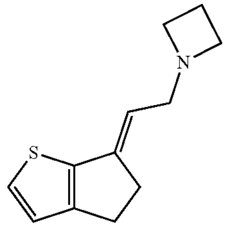 [SMILES: C(/CN1CCC1)=C1/CCc2ccsc21] |
| 67 | 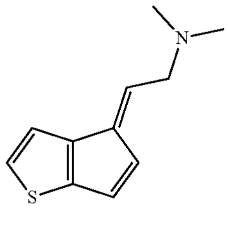 |

TABLE 1-continued
| Compound Number | Structure |
|---|---|
| 68 | 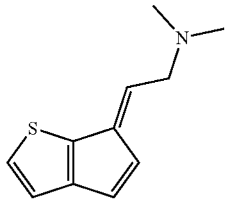 |
| 69 | 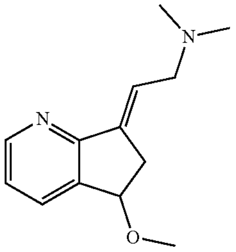 [SMILES: COC1C/C(=C\CN(C)C)c2ncccc21] |
| 70 | 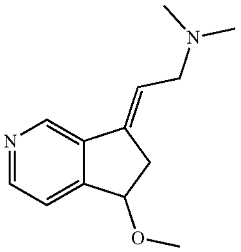 [SMILES: COC1C/C(=C\CN(C)C)c2cnccc21] |
| 71 | 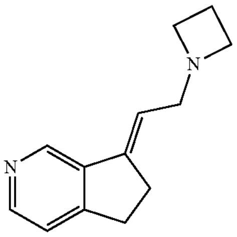 [SMILES: C(/CN1CCC1)=C1/CCc2ccncc21] |
| 72 | 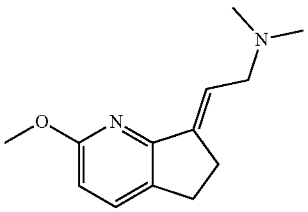 |
| 73 | 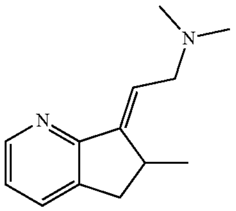 |
TABLE 1-continued
| Compound Number | Structure |
|---|---|
| 74 | 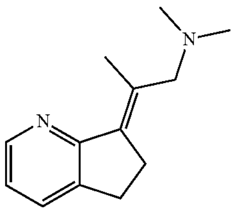 |
| 75 | 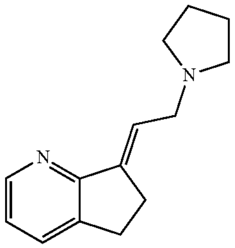 [SMILES: C(/CN1CCCC1)=C1/CCc2cccnc21] |
| 76 | 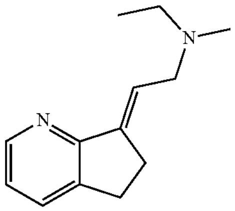 |
| 77 | 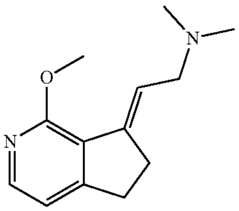 [SMILES: COc1nccc2c1/C(=C/CN(C)C)CC2] |
| 78 | 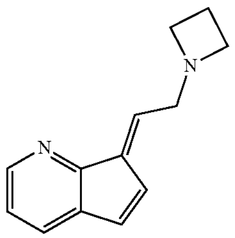 [SMILES: C1=Cc2cccnc2/C1=C/CN1CCC1] |
| 79 | 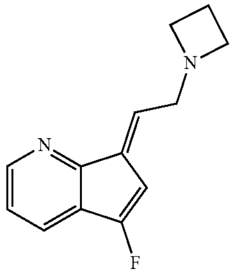 [SMILES: FC1=C/C(=C\CN2CCC2)c2ncccc21] |

TABLE 1-continued
| Compound Number | Structure |
|---|---|
| 80 | 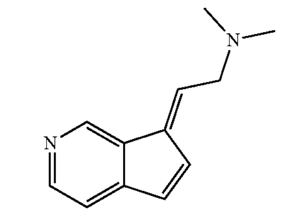 |
| 81 | 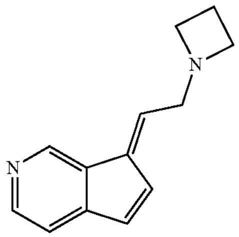 [SMILES: C1=Cc2ccncc2/C1=C/CN1CCC1] |
| 82 | 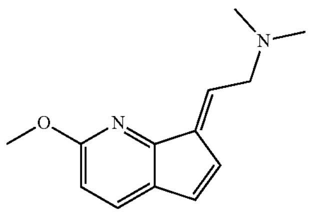 |
| 83 | 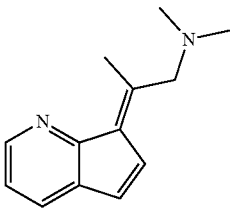 |
| 84 | 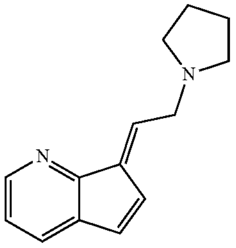 [SMILES: C1=Cc2cccnc2/C1=C/CN1CCCC1] |
| 85 | 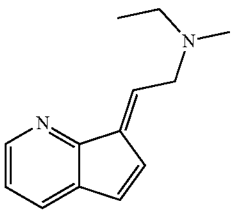 |
TABLE 1-continued
| Compound Number | Structure |
|---|---|
| 86 | 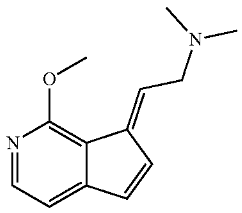 [SMILES: COc1nccc2c1/C(=C/CN(C)C)C=C2] |
| 87 | 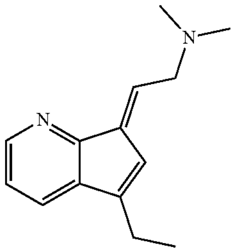 [SMILES: CCC1=C/C(=C\CN(C)C)c2ncccc21] |
| 88 | 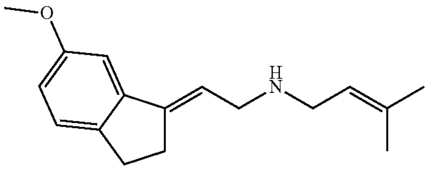 [SMILES: COc1ccc2c(c1)/C(=C/CNCC=C(C)C)CC2] |
| 89 | 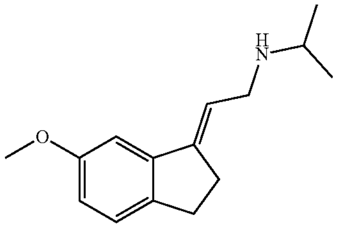 [SMILES: COc1ccc2c(c1)/C(=C/CNC(C)C)CC2] |
| 90 | 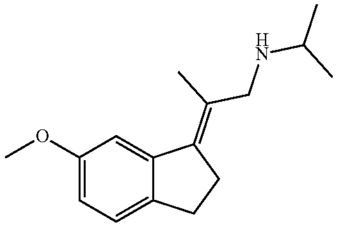 [SMILES: COc1ccc2c(c1)/C(=C(\C)CNC(C)C)CC2] |
| 91 | 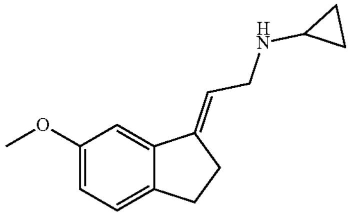 [SMILES: COc1ccc2c(c1)/C(=C/CNC1CC1)CC2] |
| 92 | 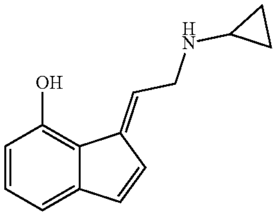 [SMILES: Oc1cccc2c1/C(=C/CNC1CC1)C=C2] |

TABLE 1-continued
| Compound Number | Structure |
|---|---|
| 93 | 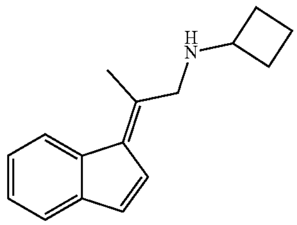 [SMILES: C/C(CNC1CCC1)=C1/C=Cc2ccccc21] |
| 94 | 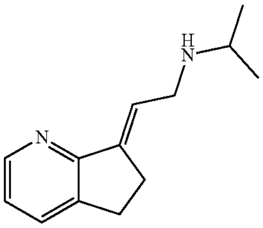 |
| 95 | 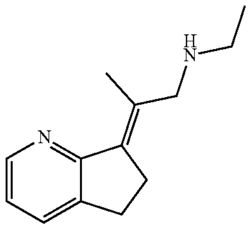 |
| 96 | 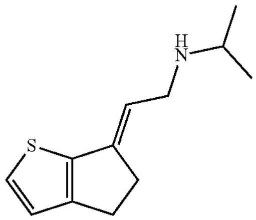 |
| 97 | 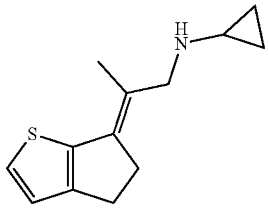 |
| 98 | 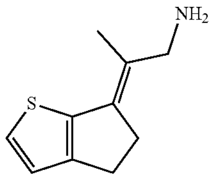 |
| 99 | 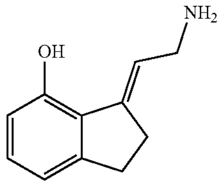 [SMILES: NC/C=C1\CCc2cccc(O)c21] |
TABLE 1-continued
| Compound Number | Structure |
|---|---|
| 100 | 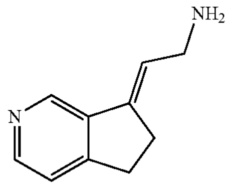 [SMILES: NC/C=C1\CCc2ccncc21] |
| 101 | 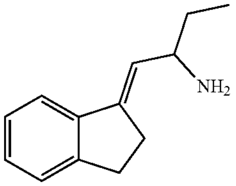 |
| 102 | 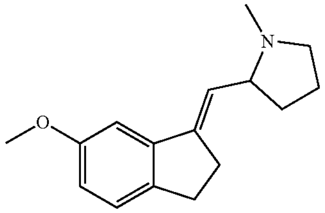 [SMILES: COc1ccc2c(c1)/C(=C/C1CCCN1C)CC2] |
| 103 | 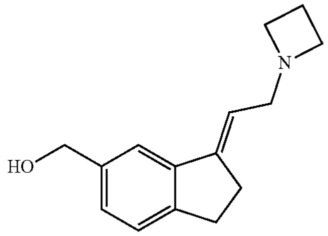 [SMILES: OCc1ccc2c(c1)/C(=C/CN1CCC1)CC2] |
| 104 | 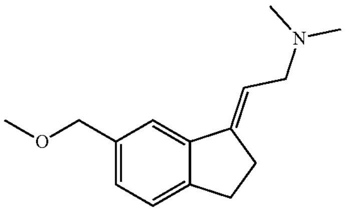 |
| 105 | 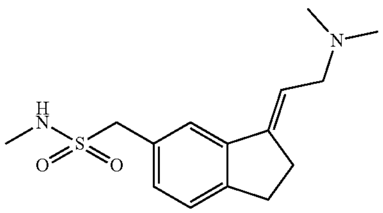 |
| 106 | 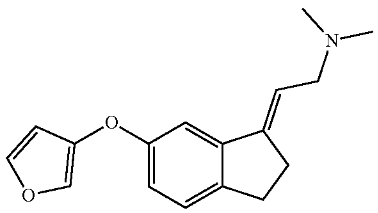 [SMILES: CN(C)C/C=C1\CCc2ccc(Oc3ccoc3)cc21] |

TABLE 1-continued
| Compound Number | Structure |
|---|---|
| 107 | 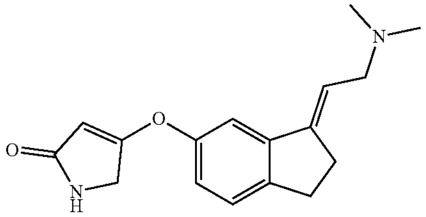 [SMILES: CN(C)C/C=C1\CCc2ccc(OC3=CC(=O)NC3)cc21] |
| 108 | 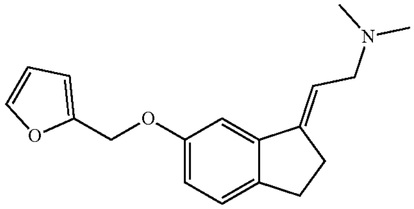 [SMILES: CN(C)C/C=C1\CCc2ccc(OCc3ccco3)cc21] |
| 109 | 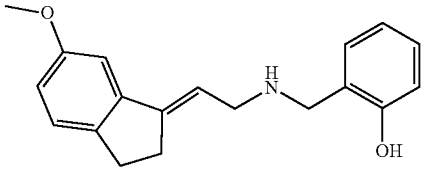 [SMILES: COc1ccc2c(c1)/C(=C/CNCc1ccccc1O)CC2] |
| 110 | 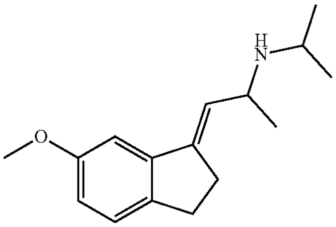 [SMILES: COc1ccc2c(c1)/C(=C/C(C)NC(C)C)CC2] |
| 111 | 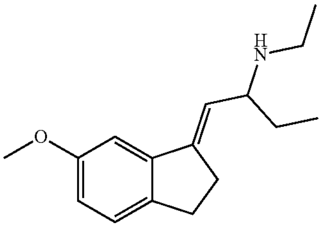 [SMILES: CCNC(/C=C1\CCc2ccc(OC)cc21)CC] |
| 112 | 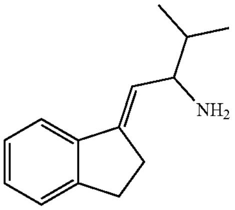 |
| 113 | 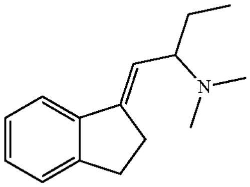 [SMILES: CCC(/C=C1\CCc2ccccc21)N(C)C] |
TABLE 1-continued
| Compound Number | Structure |
|---|---|
| 114 | 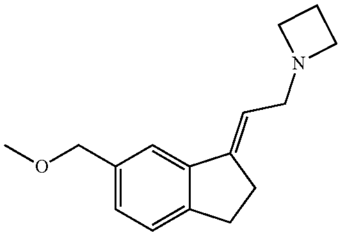 [SMILES: COCc1ccc2c(c1)/C(=C/CN1CCC1)CC2] |
| 115 | 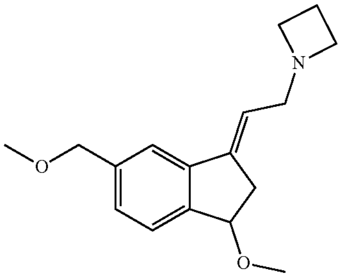 [SMILES: COCc1ccc2c(c1)/C(=C/CN1CCC1)CC2OC] |
| 116 | 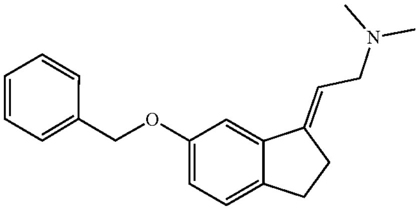 [SMILES: CN(C)C/C=C1\CCc2ccc(OCc3ccccc3)cc21] |
| 117 | 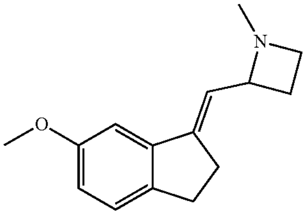 [SMILES: COc1ccc2c(c1)/C(=C/C1CCN1C)CC2] |
| 118 | 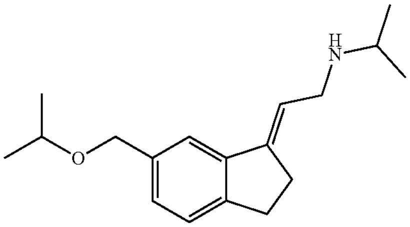 [SMILES: CC(C)NC/C=C1\CCc2ccc(COC(C)C)cc21] |
| 119 | 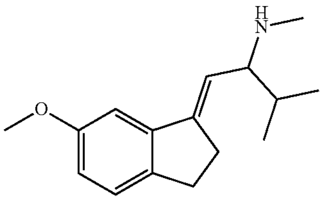 [SMILES: CNC(/C=C1\CCc2ccc(OC)cc21)C(C)C] |

TABLE 1-continued
| Compound Number | Structure |
|---|---|
| 120 | 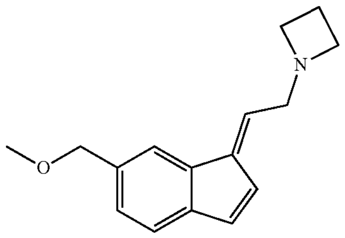 [SMILES: COCc1ccc2c(c1)/C(=C/CN1CCC1)C=C2] |
| 121 | 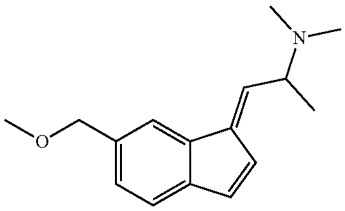 |
| 122 | 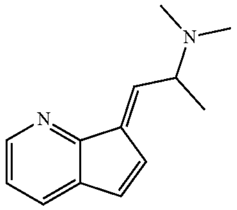 |
| 123 | 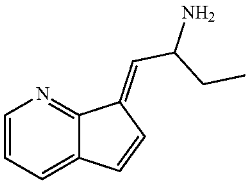 |
| 124 | 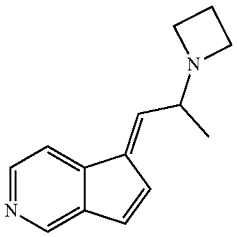 [SMILES: CC(/C=C1\C=Cc2cnccc21)N1CCC1] |
| 125 | 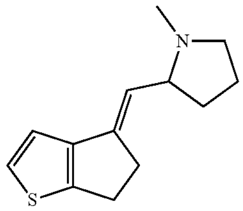 |
| 126 | 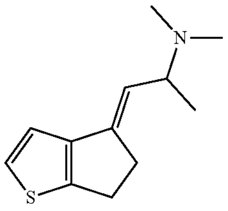 |
TABLE 1-continued
| Compound Number | Structure |
|---|---|
| 127 | 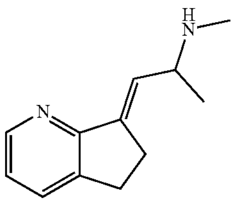 |
| 128 | 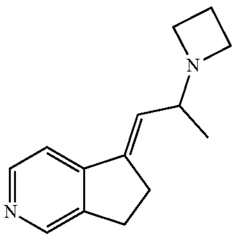 [SMILES: CC(/C=C1\CCc2cnccc21)N1CCC1] |
| 129 | 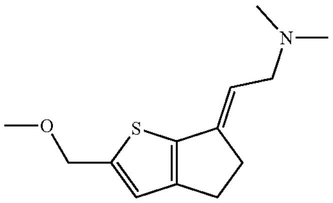 |
| 130 | 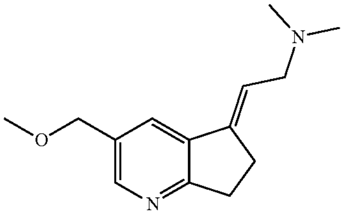 |
| 131 | 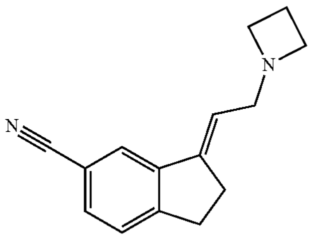 [SMILES: N#Cc1ccc2c(c1)/C(=C/CN1CCC1)CC2] |
| 132 | 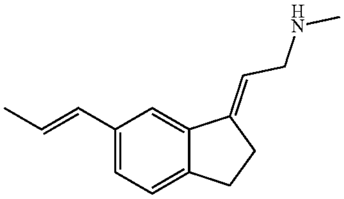 [SMILES: C/C=C/c1ccc2c(c1)/C(=C/CNC)CC2] |
| 133 | 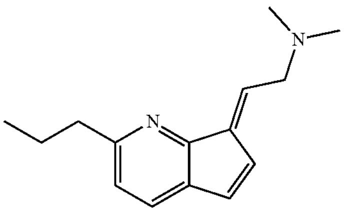 [SMILES: CCCc1ccc2c(n1)/C(=C/CN(C)C)C=C2] |

TABLE 1-continued

| Compound Number | Structure |
|---|---|
| 134 | 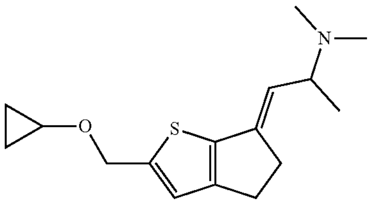 [SMILES: CC(/C=C1\CCc2cc(COC3CC3)sc21)N(C)C] |
| 135 | 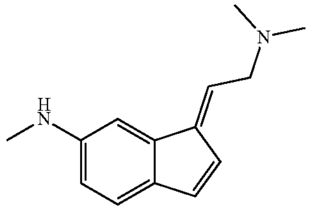 |

EXAMPLES

Example 1: Compound 5—N,N-Dimethyl[(E)-2-(6-methoxy-1-indanylidene)ethyl]amine

Compound No. 5 has been synthesized according to the following synthesis and measured to have the following percent (5-HT) activity at 5-HT2A (30 μM) shown in Table 2.

TABLE 2

| Compound No. | Structure | Percent (5-HT) Activity at 5-HT2A (30 μM) |
|---|---|---|
| 5 | 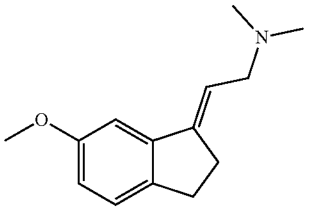 | 92 |

Scheme 1

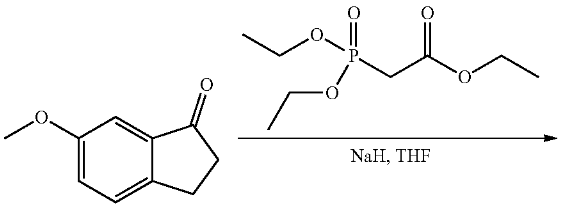

5-1

-continued

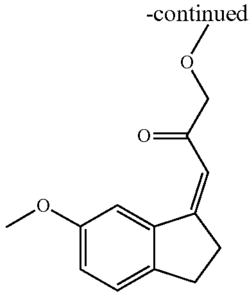

5-2b

+

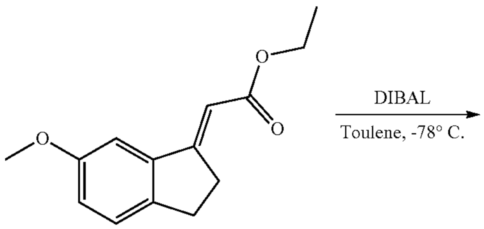

5-2a

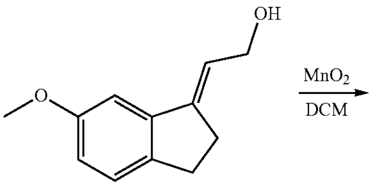

5-3

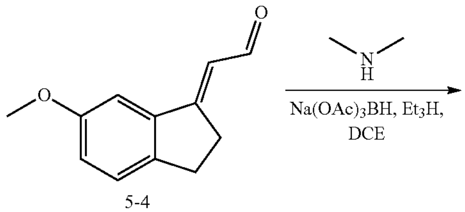

5-4

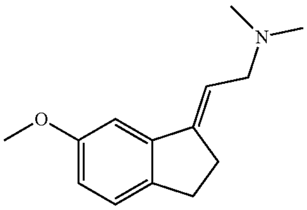

5

Procedure for the Synthesis of Compound 5-2a Ethyl-(E)-(6-methoxy-1-indanylidene)acetate Triethyl phosphonoacetate (1.47 ml, 7.40 mmol) was added dropwise to the suspension of NaH (296 mg, 12.33 mmol) in dry THF at 0° C. The reaction mixture was stirred for 1 h, under Ar atm. A solution of compound 5-1 (1 g, 6.165 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 5-2a E-isomer (377 mg, 26.3% yield); 5-2b Z-isomer (26 mg, 1.8% yield) and unreacted SM recovered (~510 mg).

m/z=233.7 $[M+H]^+$.

$^1$H NMR (300 MHZ) ($CDCl_3$) δ (ppm): 1.54 (t, J=7.4 Hz, 3H); 3.16-3.25 (m, 2H); 3.47-3.55 (m, 2H); 4.03 (s, 3H); 4.44 (q, J=6.9 Hz, 2H); 6.47 (t, J=2.7 Hz, 1H); 7.12-7.19 (m, 1H); 7.25 (d, J=2.4 Hz, 1H); 7.44 (d, J=8.2 Hz, 1H).

Procedure for the Synthesis of Compound 5-3 (E)-2-(6-Methoxy-1-indanylidene)ethanol To a solution of compound 5-2a (100 mg, 0.43 mmol) in dry toluene (1 mL) under nitrogen atmosphere, a solution of 1.0 M diisobutylaluminium hydride (DIBAL-H) (0.86 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 5-3 (78 mg, 95.2% yield).

m/z=191.6 $[M+H]^+$.

$^1$H NMR (300 MHZ) ($CDCl_3$) δ (ppm): 1.85 (bs, 1H); 2.91-3.02 (m, 2H); 3.03-3.11 (m, 2H); 4.01 (s, 3H); 4.73 (d, J=6.6 Hz, 2H); 5.93-6.00 (m, 1H); 6.97-7.04 (m, 1H); 7.25 (d, J=2.3 Hz, 1H); 7.38 (d, J=8.3 Hz, 1H).

Procedure for the Synthesis of Compound 5-4 (E)-(6-Methoxy-1-indanylidene)acetaldehyde A solution of alcohol 5-3 (200 mg, 1.06 mmol) and $MnO_2$ (230.9 mg, 2.66 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 5-4 (180 mg, 91% yield).

m/z=189.7 $[M+H]^+$.

$^1$H NMR (300 MHZ) ($CDCl_3$) δ (ppm): 3.15-3.33 (m, 2H); 3.44-3.56 (m, 2H); 4.03 (s, 3H); 6.60-6.68 (m, 1H); 7.17-7.29 (m, 2H); 7.46 (d, J=8.4 Hz, 1H); 10.24 (d, J=8.1 Hz, 1H).

Procedure for the Synthesis of Compound 5 N,N-Dimethyl[(E)-2-(6-methoxy-1-indanylidene)ethyl] amine To the solution of compound 5-4 (50 mg, 0.27 mmol) in DCE was added dimethylamine hydrochloride (43.32 mg, 0.531 mmol), along with $Et_3N$ (0.075 ml, 0.53 mmol). The reaction mixture was stirred at room temperature for 1 h. Then, $Na(OAc)_3BH$ (112.75 mg, 0.53 mmol) was added and the reaction mixture was stirred at room temperature for overnight. The crude was extracted with EtOAc, organic layer was dried over $Na_2SO_4$, filtered and concentrated. The crude was purified by column chromatography using DCM: MeOH as eluent to give the desired product 5 (180 mg, 91% yield).

m/z=218.8 $[M+H]^+$.

$^1$H NMR (300 MHZ) ($CDCl_3$) δ (ppm): 2.75 (s, 6H); 3.00-3.21 (m, 4H); 3.33 (m, 2H); 3.87 (s, 3H); 6.30-6.35 (m, 1H); 6.75-6.82 (m, 1H); 7.02 (d, J=2.4 Hz, 1H); 7.33 (d, J=8.2 Hz, 1H).

E and Z Configurations of Compound 1

Compound 5, described here with structure shown in Scheme 1, is the stable E isomer. However, the initial reaction in Scheme 1 with compound 5-1 produces both the E and Z isomers of 5-2b. Column chromatography was used to separate the isomers and each isomer was then carried through the next three reactions separately, to produce both compound 5 and its Z isomer. The Z isomer is less stable, with 40% (by NMR) of the Z isomer of compound 5-4 converting to the E isomer, shortly following synthesis.

Example 2: Compound 10—N,N-Dimethyl[(Z)-2-(6-methoxy-1-indanylidene)-2-fluoroethyl]amine

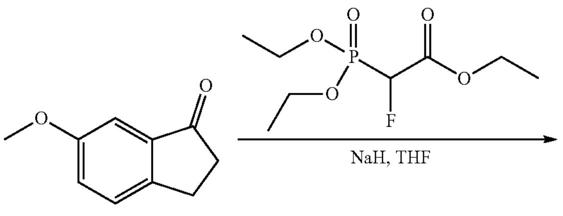

10-1

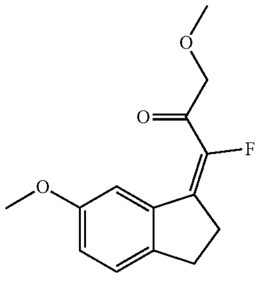

10-2a

+

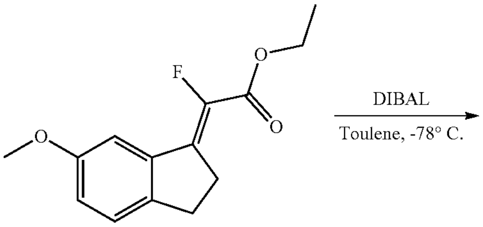

10-2b

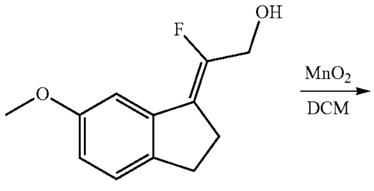

10-3

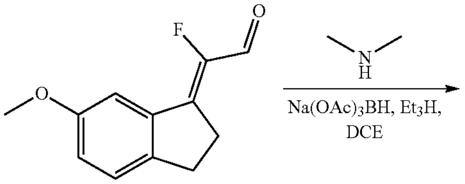

10-4

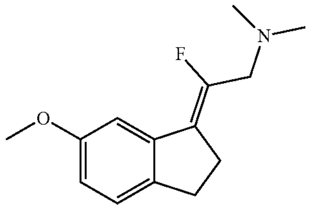

10

Procedure for the Synthesis of Compound 10-2b Ethyl-(Z)-(6-methoxy-1-indanylidene)fluoroacetate Triethyl phosphonoacetate (1.792 g, 7.4 mmol) was added dropwise to the suspension of NaH (493.3 mg, 20.55 mmol) in dry THF at 0° C. The reaction mixture was stirred for 1 h, under Ar atm. A solution of compound 10-1 (1 g, 6.2 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 10-2a E-isomer (241 mg, 15.6% yield); 10-2b Z-isomer (38 mg, 2.5% yield) and unreacted SM recovered (~510 mg).

m/z=251.7 $[M+H]^+$.

$^1H$ NMR (300 MHZ) ($CDCl_3$) δ (ppm): 1.39 (t, J=7.1 Hz, 3H); 2.99-3.07 (m, 2H); 3.17-3.26 (m, 2H); 3.82 (s, 3H); 4.34 (q, J=7.4 Hz, 2H); 6.88-6.98 (m, 1H); 7.22 (d, J=8.6 Hz, 1H); 7.46 (d, J=2.74 Hz, 1H).

$^{19}F$ NMR (300 MHZ) ($CDCl_3$) δ (ppm): −130.8.

Procedure for the Synthesis of Compound 10-3 (Z)-2-(6-Methoxy-1-indanylidene)-2-fluoroethanol To a solution of compound 10-2b (240 mg, 0.94 mmol) in dry toluene (1 mL) under nitrogen atmosphere, a solution of 1.0 M diisobutylaluminium hydride (DIBAL-H) (1.88 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 10-3 (197 mg, 98.6% yield).

m/z=209.7 $[M+H]^+$.

$^1H$ NMR (300 MHZ) ($CDCl_3$) δ (ppm): 2.79-2.91 (m, 2H); 2.98-3.09 (m, 2H); 3.78 (s, 3H); 4.38 (s, 1H); 4.45 (s, 1H); 6.64-6.90 (m, 1H); 7.25 (d, J=2.4 Hz, 1H); 7.44 (d, J=8.0 Hz, 1H).

$^{19}F$ NMR (300 MHZ) ($CDCl_3$) δ (ppm): −119.2.

Procedure for the Synthesis of Compound 10-4 (Z)-(6-Methoxy-1-indanylidene)fluoroacetaldehyde A solution of alcohol 10-3 (150 mg, 0.72 mmol) and $MnO_2$ (626.3 mg, 7.2 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 10-4 (100 mg, 67.3% yield).

m/z=207.7 $[M+H]^+$.

$^1H$ NMR (300 MHZ) ($CDCl_3$) δ (ppm): 3.06-3.18 (m, 2H); 3.19-3.33 (m, 2H); 3.84 (s, 3H); 6.96-7.04 (m, 1H); 7.28 (d, J=8.5 Hz, 1H); 7.48 (d, J=2.5 Hz, 1H); 9.73 (d, J=14.9 Hz, 1H).

$^{19}F$ NMR (300 MHz) ($CDCl_3$) δ (ppm): −136.4.

Procedure for the Synthesis of Compound 10 N,N-Dimethyl[(Z)-2-(6-methoxy-1-indanylidene)-2-fluoroethyl]amine To the solution of compound 10-4 (156 mg, 0.76 mmol) in DCE was added dimethylamine hydrochloride (92.5 mg, 1.13 mmol), along with $Et_3N$ (0.21 ml, 1.51 mmol). The reaction mixture was stirred at room temperature for 1 h. Then, $Na(OAc)_3BH$ (320.5 mg, 1.51 mmol) was added and the reaction mixture was stirred at room temperature for overnight. The crude was extracted with EtOAc, organic layer was dried over $Na_2SO_4$, filtered and concentrated. The crude was purified by column chromatography using DCM: MeOH as eluent to give the desired product 10 (20 mg, 11.2% yield).

m/z=236.8 $[M+H]^+$.

$^1H$ NMR (300 MHZ) ($CDCl_3$) δ (ppm): 2.22 (s, 6H); 2.56-2.68 (m, 2H); 2.78-2.89 (m, 2H); 3.03 (s, 1H); 3.11 (s, 1H); 3.69 (s, 3H); 6.62-6.71 (m, 1H); 7.01 (d, J=8.7 Hz, 1H); 7.26 (d, J=2.5 Hz, 1H).

$^{19}F$ NMR (300 MHZ) ($CDCl_3$) δ (ppm): −109.7.

Example 3: Compound 12—1-[(E)-2-(6-Methoxy-1-indanylidene)ethyl]azetidine

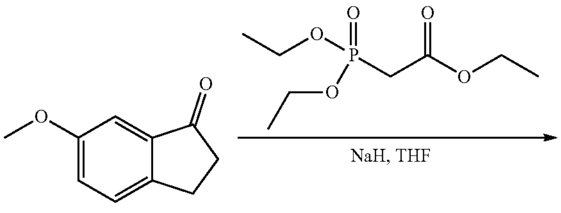

12-1

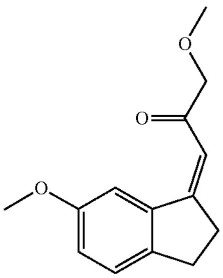

12-2b

+

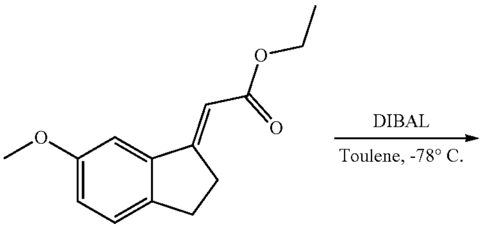

12-2a

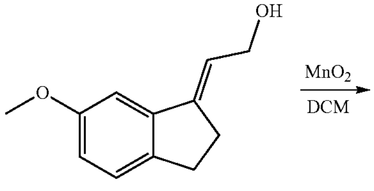

12-3

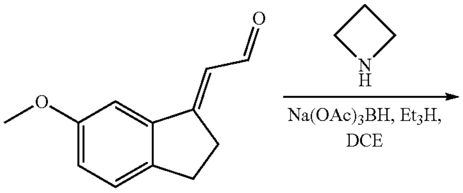

12-4

-continued

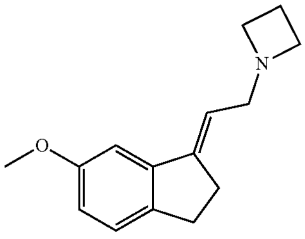

12

Similar Synthetic Procedure as for Compound 5 Synthesis

Procedure for the Synthesis of Compound 12 1-[(E)-2-(6-Methoxy-1-indanylidene)ethyl]azetidine To the solution of compound 12-4 (79.6 mg, 0.42 mmol) in DCE was added azetidine (59.4 mg, 0.634 mmol), along with $Et_3N$ (0.12 ml, 0.82 mmol). The reaction mixture was stirred at room temperature for 1 h. Then, $Na(OAc)_3BH$ (179.4 mg, 0.82 mmol) was added and the reaction mixture was stirred at room temperature for overnight. The crude was extracted with EtOAc, organic layer was dried over $Na_2SO_4$, filtered and concentrated. The crude was purified by column chromatography using DCM:MeOH as eluent to give the desired product 12 (20 mg, 21% yield).

m/z=230.8 $[M+H]^+$.

$^1$H NMR (300 MHZ) ($CDCl_3$) δ (ppm): 2.65-2.87 (m, 2H); 3.05-3.18 (m, 2H); 3.18-3.30 (m, 2H); 4.00-3.99 (m, 2H); 4.07 (s, 3H); 4.18-4.30 (m, 2H); 6.12-6.25 (m, 1H); 7.05-7.15 (m, 1H); 7.26 (d, J=2.7 Hz, 1H); 7.43 (d, J=7.8 Hz, 1H).

Example 4: Compounds 14 and 24—N,N-Dimethyl [(E)-2-(3-oxa-1,2,6,7-tetrahydro-as-indacen-8-ylidene) ethyl]amine and 1-[(E)-2-(3-Oxa-1,2,6,7-tetrahydro-as-indacen-8-ylidene)ethyl]azetidine

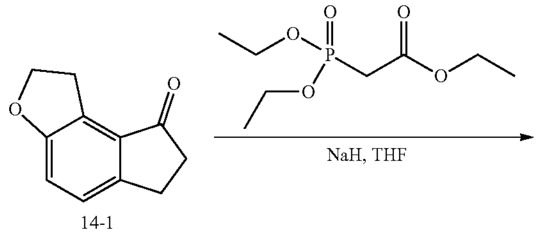

14-1

-continued

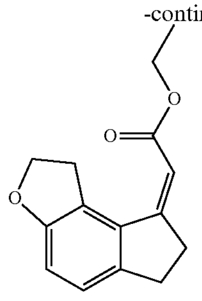

14-2b

+

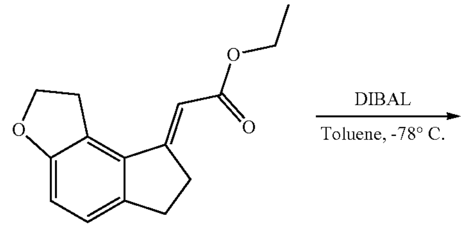

14-2a

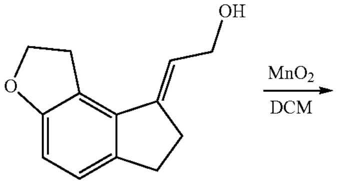

14-3

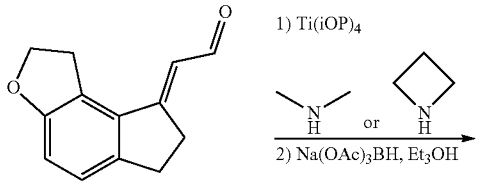

14-4

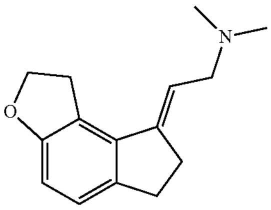

or

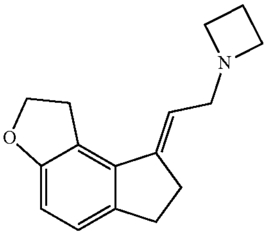

14

24

Procedure for the Synthesis of Compound 14-2a Ethyl-(E)-(3-oxa-1,2,6,7-tetrahydro-as-indacen-8-ylidene)acetate Triethyl phosphonoacetate (1.544 g, 6.89 mmol) was added dropwise to the suspension of NaH (276 mg, 11.5 mmol) in dry THF at 0° C. The reaction mixture was stirred for 1 h, under Ar atm. A solution of compound 14-1 (1 g, 5.74 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex:

EtOAc as eluent to give desired product 14-2a E-isomer (218 mg, 15.5% yield); 14-2b Z-isomer (86 mg, 6.1% yield).

m/z=245.7 $[M+H]^+$.

$^1H$ NMR (300 MHZ) ($CDCl_3$) δ (ppm): 1.54 (t, J=7. Hz, 2H); 3.11-3.22 (m, 2H); 3.44-3.53 (m, 2H); 3.55 (t, J=8.8 Hz, 2H); 4.41 (q, J=7.1 Hz, 2H); 4.81 (q, J=8.8 Hz, 2H); 6.27 (t, J=2.7 Hz, 1H); 6.99 (d, J=8.5 Hz, 2H); 7.27 (d, J=8.2 Hz, 1H).

Procedure for the Synthesis of Compound 14-3 (E)-2-(3-Oxa-1,2,6,7-tetrahydro-as-indacen-8-ylidene)ethanol To a solution of compound 14-2a (218 mg, 0.89 mmol) in dry toluene (1 mL) under nitrogen atmosphere, a solution of 1.0 M diisobutylaluminium hydride (DIBAL-H) (1.8 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 14-3 (179 mg, 99.4% yield).

m/z=203.8 $[M+H]^+$.

$^1H$ NMR (300 MHZ) ($CDCl_3$) δ (ppm): 1.85 (bs, 1H); 2.96-3.12 (m, 2H); 3.13-3.26 (m, 2H); 3.56 (t, J=8.8 Hz, 2H); 4.61 (d, J=7.1 Hz, 2H); 4.86 (t, J=8.8 Hz, 2H); 6.13-6.23 (m, 1H); 6.96 (d, J=8.3 Hz, 1H); 7.27 (d, J=8.3 Hz, 1H).

Procedure for the Synthesis of Compound 14-4 (E)-(3-Oxa-1,2,6,7-tetrahydro-as-indacen-8-ylidene) acetaldehyde A solution of alcohol 14-3 (200 mg, 0.99 mmol) and $MnO_2$ (859.7 mg, 9.88 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 14-4 (121 mg, 61% yield).

m/z=201.7 $[M+H]^+$.

$^1H$ NMR (300 MHZ) ($CDCl_3$) δ (ppm): 3.16-3.31 (m, 2H); 3.37-3.48 (m, 2H); 3.51 (t, J=8.7 Hz, 2H); 4.81 (t, J=8.7 Hz, 2H); 6.41-6.51 (m, 1H); 7.03 (d, J=8.5 Hz, 1H); 7.27 (d, J=8.5 Hz, 1H); 10.18 (d, J=7.8 Hz, 1H).

Procedure for the Synthesis of Compound 24 1-[(E)-2-(3-Oxa-1,2,6,7-tetrahydro-as-indacen-8-ylidene)ethyl]azetidine To the solution of compound 14-4 (50 mg, 0.25 mmol) was added $Ti(OiPr)_4$ (0.15 ml, 0.5 mmol). The reaction mixture was stirred at room temperature for 1 h. Then, added azetidine (15.68 mg, 0.27 mmol) and the reaction was stirred at rt for overnight. EtOH (2 ml) and $Na(OAc)_3BH$ (106 mg, 0.5 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 24 (10 mg, 16.5% yield).

m/z=242.8 $[M+H]^+$.

$^1H$ NMR (300 MHZ) ($CDCl_3$) δ (ppm): 2.04-2.23 (m, 2H); 2.69-2.82 (m, 2H); 2.87-2.98 (m, 2H); 3.23-3.38 (m, 7H); 4.63 (t, J=8.8 Hz, 2H); 5.64-5.73 (m, 1H); 6.66 (d, J=7.6 Hz, 1H); 6.98 (d, J=7.8 Hz, 1H).

Procedure for the Synthesis of Compound 14 N,N-Dimethyl[(E)-2-(3-oxa-1,2,6,7-tetrahydro-as-indacen-8-ylidene)ethyl]amine To the solution of compound 14-4 (46 mg, 0.23 mmol) was added $Ti(OiPr)_4$ (0.14 ml, 0.46 mmol). The reaction mixture was stirred at room temperature for 1 h. Then, added dimethylamine (20.7 mg, 0.46 mmol) and the reaction was stirred at rt for overnight. EtOH (2 ml) and $Na(OAc)_3BH$ (97.52 mg, 0.46 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 14 (10 mg, 19% yield).

m/z=230.8 $[M+H]^+$.

$^1H$ NMR (300 MHZ) ($CDCl_3$) δ (ppm): 2.37 (s, 6H); 2.69-2.82 (m, 2H); 2.89-2.98 (m, 2H); 3.18 (d, J=7.4 Hz, 2H); 3.32 (t, J=8.4 Hz, 2H); 4.61 (t, J=8.6 Hz, 2H); 5.81-5.89 (m, 1H); 6.67 (d, J=8.2 Hz, 1H); 7.00 (d, J=8.4 Hz, 1H).

Example 5: Compound 22—N,N-Dimethyl[(E)-2-(1-indenylidene)ethyl]amine

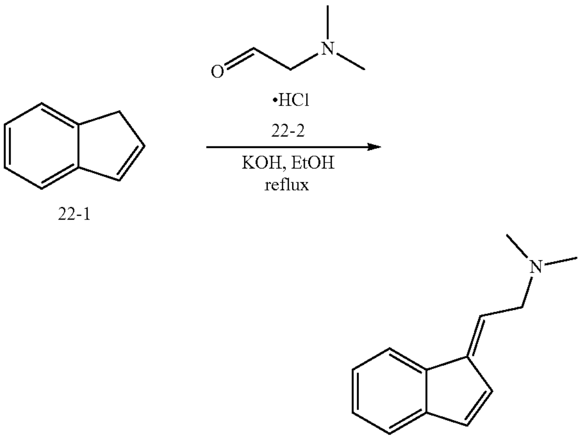

22-1

22

Procedure for the Synthesis of Compound 22 N,N-Dimethyl[(E)-2-(1-indenylidene)ethyl]amine Compound 22-1 (200 mg, 1.72 mmol) was dissolved in 1% KOH solution in EtOH and then added compound 22-2 (212.6 mg, 1.72 mmol). The reaction mixture was heated at 70° C. for 2 days. Solvent was evaporated and the crude was extracted with EtOAc, organic phase was separated, dried over $Na_2SO_4$, filtered and concentrated. The crude was purified by semi-prep HPLC using 10-100% B vs D (B=MeOH; D=0.1% formic acid) to give desired product 22.

m/z=186.3 $[M+H]^+$.

$^1H$ NMR (300 MHZ) (MeOD) δ (ppm): 2.69 (s, 6H); 3.90 (d, J=8.1 Hz, 2H); 6.63 (d, J=5.8 Hz, 1H); 6.68 (t, J=7.5 Hz, 1H); 7.01 (d, J=5.8 Hz, 1H); 7.23-7.30 (m, 2H); 7.42-7.53 (m, 1H); 7.63 (d, J=7.9 Hz, 1H); 7.82 (d, J=7.5 Hz, 1H).

Example 6: Compound 23—N,N-Dimethyl[(E)-2-(6-methoxy-1-indanylidene)-2-fluoroethyl]amine

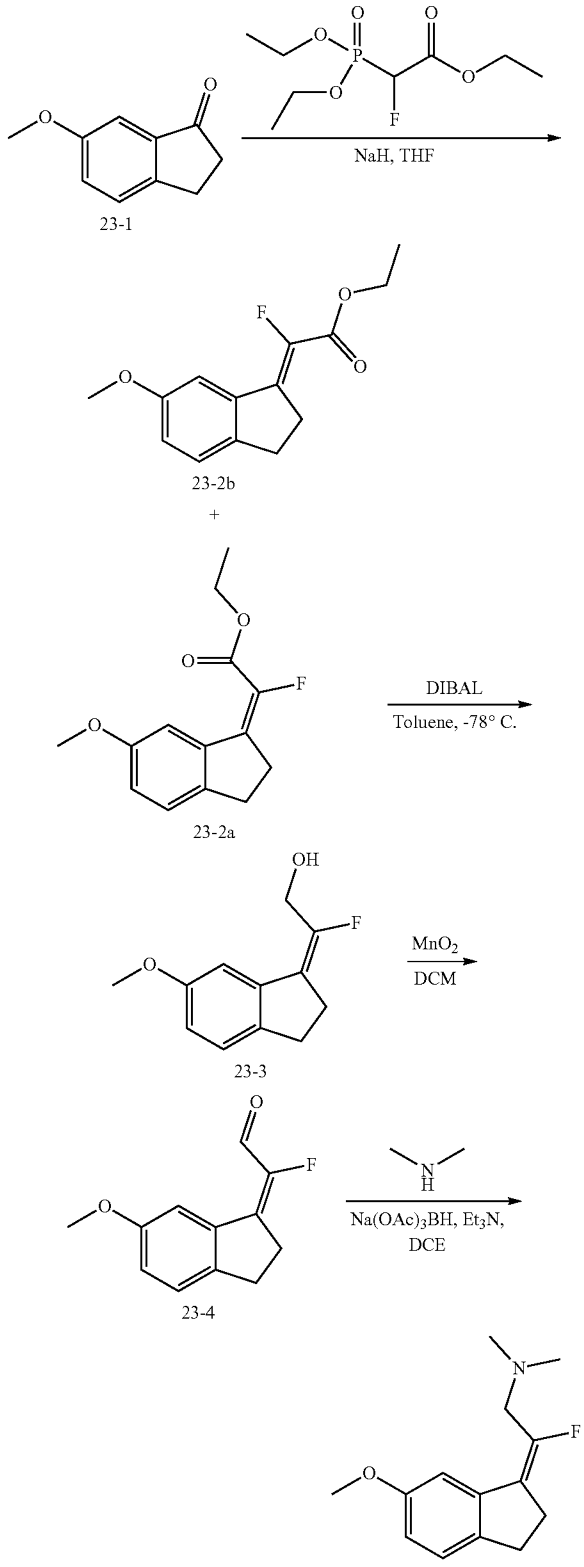

23-1

23-2b

+

23-2a 23-3

23-4

23

Procedure for the Synthesis of Compound 23-2a (E)-1-(6-Methoxy-1-indanylidene)-1-fluoro-3-methoxy-2-propanone Triethyl phosphonoacetate (1.792 g, 7.4 mmol) was added dropwise to the suspension of NaH (493.3 mg, 20.55 mmol) in dry THF at 0° C. The reaction mixture was stirred for 1 h, under Ar atm. A solution of compound 23-1 (1 g, 6.2 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 23-2a E-isomer (241 mg, 15.6% yield); 23-2b Z-isomer (38 mg, 2.5% yield).

m/z=251.8 $[M+H]^+$.

$^1$H NMR (300 MHz) ($CDCl_3$) δ (ppm): 1.39 (t, J=7.1 Hz, 3H); 2.92-3.00 (m, 2H); 3.01-3.11 (m, 2H); 3.85 (s, 3H); 4.37 (q, J=7.1 Hz, 2H); 6.88-6.98 (m, 1H); 7.12 (d, J=8.6 Hz, 1H); 8.33 (d, J=2.7 Hz, 1H).

$^{19}$F NMR (300 MHZ) ($CDCl_3$) δ (ppm): −117.7.

Procedure for the Synthesis of Compound 23-3 (E)-2-(6-Methoxy-1-indanylidene)-2-fluoroethanol To a solution of compound 23-2a (380 mg, 1.52 mmol) in dry toluene (1 mL) under nitrogen atmosphere, a solution of 1.0 M diisobutylaluminium hydride (DIBAL-H) (3.04 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 23-3 (300 mg, 94.8% yield).

m/z=209.7 $[M+H]^+$.

$^1$H NMR (300 MHZ) ($CDCl_3$) δ (ppm): 3.17 (s, 4H); 4.03 (s, 3H); 4.76-4.92 (m, 2H); 7.06-7.14 (m, 1H); 7.25 (d, J=2.4 Hz, 1H); 7.44 (d, J=8.0 Hz, 1H).

$^{19}$F NMR (300 MHZ) ($CDCl_3$) δ (ppm): −107.2.

Procedure for the Synthesis of Compound 23-4 (E)-(6-Methoxy-1-indanylidene)fluoroacetaldehyde A solution of alcohol 23-3 (183 mg, 0.88 mmol) and $MnO_2$ (764 mg, 8.8 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 23-4 (130 mg, 71.3% yield).

m/z=207.8 $[M+H]^+$.

$^1$H NMR (300 MHZ) ($CDCl_3$) δ (ppm): 2.99-3.06 (m, 2H); 3.06-3.15 (m, 2H); 3.84 (s, 3H); 6.96-7.04 (m, 1H); 7.28 (s, 1H); 7.42 (d, J=2.5 Hz, 1H); 10.03 (d, J=16.4 Hz, 1H).

$^{19}$F NMR (300 MHz) ($CDCl_3$) δ (ppm): −126.8.

Procedure for the Synthesis of Compound 23 N,N-Dimethyl[(E)-2-(6-methoxy-1-indanylidene)-2-fluoroethyl]amine To the solution of compound 23-4 (89.4 mg, 0.43 mmol) in DCE was added dimethylamine hydrochloride (53.03 mg, 0.65 mmol), along with $Et_3N$ (0.12 ml, 0.87 mmol). The reaction mixture was stirred at room temperature for 1 h. Then, $Na(OAc)_3BH$ (183.6 mg, 0.87 mmol) was added and the reaction mixture was stirred at room temperature for overnight. The crude was extracted with EtOAc, organic layer was dried over $Na_2SO_4$, filtered and concentrated. The crude was purified by column chromatography using DCM: MeOH as eluent to give the desired product 23 (6 mg, 5.9% yield).

m/z=236.8 $[M+H]^+$.

$^1$H NMR (300 MHz) ($CDCl_3$) δ (ppm): 2.83 (s, 6H); 2.89 (s, 4H); 3.38 (s, 1H); 3.45 (s, 1H); 3.82 (s, 1H); 6.74-6.79 (m, 1H); 7.08 (d, J=2.6 Hz, 1H); 7.15 (d, J=8.2 Hz, 1H).

$^{19}$F NMR (300 MHZ) ($CDCl_3$) δ (ppm): −93.6.

Example 7: Compounds 25 and 26-1-[(E)-2-(5-Methoxy-1-indanylidene)ethyl]azetidine and N,N-Dimethyl[(E)-2-(5-methoxy-1-indanylidene)ethyl] amine

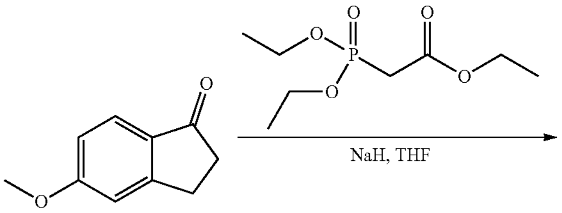

25-1

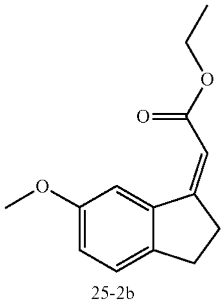

25-2b

+

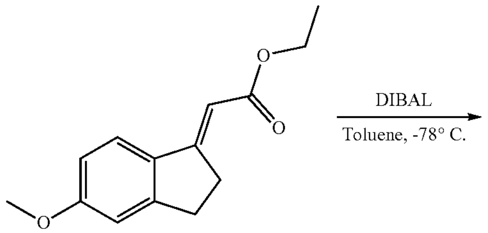

25-2a

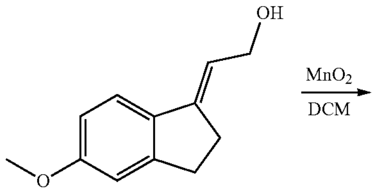

25-3

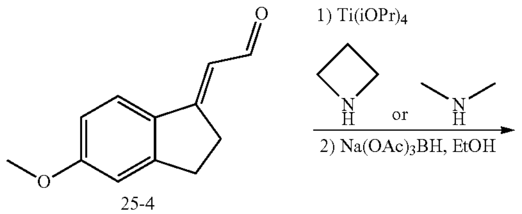

25-4

-continued

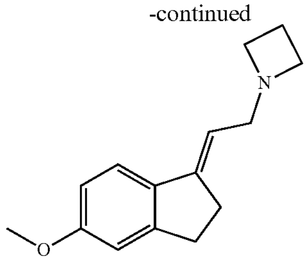

25 or

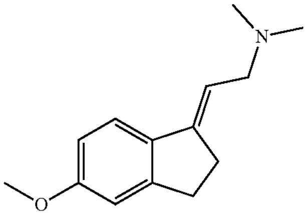

26

Procedure for the Synthesis of Compound 25-2a Ethyl-(E)-(5-methoxy-1-indanylidene)acetate Triethyl phosphonoacetate (1.66 g, 7.39 mmol) was added dropwise to the suspension of NaH (296.2 mg, 12.34 mmol) in dry THF at 0° C. The reaction mixture was stirred for 1 h, under Ar atm. A solution of compound 25-1 (1 g, 6.17 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 25-2a E-isomer (560 mg, 39.2% yield); 25-2b Z-isomer (110 mg, 7.5% yield).

m/z=233.7 $[M+H]^+$.

$^1$H NMR (300 MHZ) ($CDCl_3$) δ (ppm): 1.31 (t, J=7.2 Hz, 3H); 2.95-3.07 (m, 2H); 3.21-3.31 (m, 2H); 3.80 (s, 3H); 4.19 (q, J=6.7 Hz, 2H); 6.14 (t, J=2.4 Hz, 1H); 6.78-6.84 (m, 2H); 7.47 (d, J=8.4 Hz, 1H).

Procedure for the Synthesis of Compound 25-3 (E)-2-(5-Methoxy-1-indanylidene)ethanol To a solution of compound 25-2a (560 mg, 2.41 mmol) in dry toluene (1 mL) under nitrogen atmosphere, a solution of 1.0 M diisobutylaluminium hydride (DIBAL-H) (4.8 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 3 (white solid, 457 mg, 99.5% yield).

m/z=191.6 $[M+H]^+$.

$^1$H NMR (300 MHZ) ($CDCl_3$) δ (ppm): 1.80 (bs, 1H); 2.73-2.90 (m, 2H); 3.28-3.48 (m, 2H); 3.85 (s, 3H); 4.73 (d, J=6.6 Hz, 2H); 6.17-6.22 (m, 1H); 6.78-6.84 (m, 2H); 7.47 (d, J=8.4 Hz, 1H).

Procedure for the Synthesis of Compound 25-4 (E)-(5-Methoxy-1-indanylidene)acetaldehyde A solution of alcohol 25-3 (494 mg, 2.94 mmol) and $MnO_2$ (2.25 g, 25.9 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 25-4 (152 mg, 31% yield).

m/z=189.7 $[M+H]^+$.

$^1H$ NMR (300 MHZ) ($CDCl_3$) δ (ppm): 2.96-3.14 (m, 2H); 3.18-3.33 (m, 2H); 3.83 (s, 3H); 6.32 (d, J=9.3 Hz, 1H); 6.77-6.88 (m, 2H); 7.49 (d, J=9.4 Hz, 1H); 9.93 (d, J=8.03 Hz, 1H).

Procedure for the Synthesis of Compound 25 1-[(E)-2-(5-Methoxy-1-indanylidene)ethyl]azetidine To the solution of compound 25-4 (135 mg, 0.72 mmol) was added $Ti(OiPr)_4$ (0.33 ml, 1.08 mmol). The reaction mixture was stirred at room temperature for 1 h. Then, added azetidine (45.1 mg, 0.79 mmol) and the reaction was stirred at rt for overnight. EtOH (2 ml) and $Na(OAc)_3BH$ (304 mg, 1.43 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 25 (yellow oil, 10 mg, 19% yield).

m/z=230.6 $[M+H]^+$.

$^1H$ NMR (300 MHZ) ($CDCl_3$) δ (ppm): 2.08-2.20 (m, 2H); 2.69-2.82 (m, 2H); 2.91-3.02 (m, 2H); 3.26 (d, J=7.4 Hz, 2H); 3.36 (t, J=7.4 Hz, 4H); 3.79 (s, 3H); 5.66-5.79 (m, 1H); 6.71-6.82 (m, 2H); 7.36 (d, J=8.6 Hz, 1H).

Procedure for the Synthesis of Compound 26 N,N-Dimethyl[(E)-2-(5-methoxy-1-indanylidene)ethyl] amine To the solution of compound 25-4 (74 mg, 0.393 mmol) was added $Ti(OiPr)_4$ (0.18 ml, 0.59 mmol). The reaction mixture was stirred at room temperature for 1 h. Then, added dimethylamine (35.3 mg, 0.432 mmol) and the reaction was stirred at rt for overnight. EtOH (2 ml) and $Na(OAc)_3BH$ (167 mg, 0.786 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 26 (yellow oil, 11 mg, 12.9% yield).

m/z=230.6 $[M+H]^+$.

$^1H$ NMR (300 MHZ) ($CDCl_3$) δ (ppm): 2.26 (s, 6H); 2.57-2.67 (m, 2H); 2.81-2.92 (m, 2H); 3.09 (d, J=7.6 Hz, 2H); 3.67 (s, 3H); 5.66-5.79 (m, 1H); 7.25-7.30 (m, 1H).

Example 7: Compound 27-1-[(E)-2-(6-Trifluoromethoxy-1-indanylidene)ethyl]azetidine

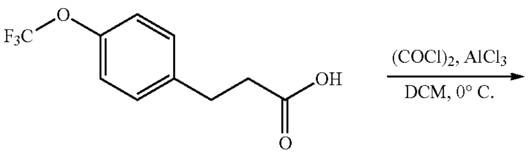

27-1

-continued

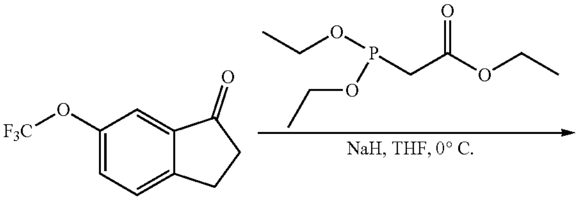

27-2

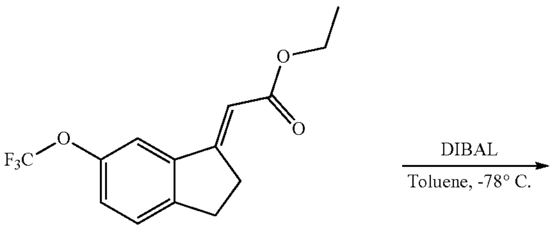

27-3

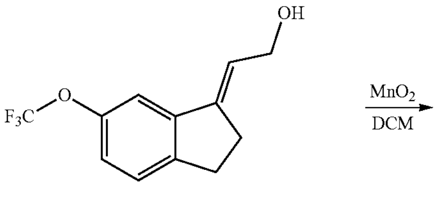

27-4

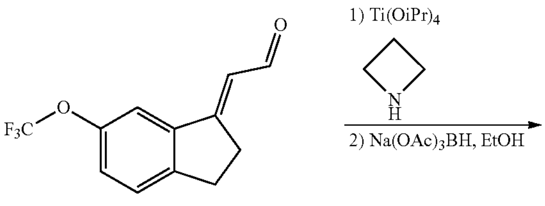

27-5

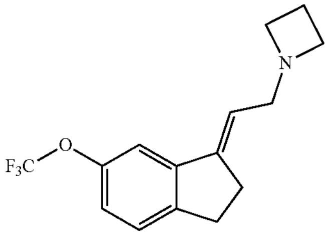

27

Procedure for the Synthesis of Compound 27-2 6-Trifluoromethoxy-1-indanone

To a solution of compound 27-1 (1 g, 4.27 mmol) in DCM at 0° C. was added a catalytic amount of DMF. Oxalyl chloride (0.72 ml, 8.67 mmol) was added dropwise to the reaction and the mixture was stirred at rt for 2 hours. Evaporate the solvent under rota evaporator and redissolved in DCM. Then, added $AlCl_3$ (1.14 g, 8.67 mmol) portion wise at 0° C., and the reaction mixture was stirred at rt for overnight. Cooled down to 0° C. and quenched with water. Extracted with DCM, organic layer was dried over $Na_2SO_4$, filtered, and concentrated to give desired product 27-2 (596 mg, 64.6% yield).

m/z=217.7 $[M+H]^+$.

$^1H$ NMR (300 MHZ) ($CDCl_3$) δ (ppm): 2.69-2.82 (m, 2H); 3.08-3.23 (m, 2H); 7.46-7.64 (m, 2H); 7.78 (d, J=2.2 Hz, 1H).

$^{19}F$ NMR (300 MHZ) ($CDCl_3$) δ (ppm): −58.0.

Procedure for the Synthesis of Compound 27-3 Ethyl-(E)-(6-trifluoromethoxy-1-indanylidene)acetate Triethyl phosphonoacetate (679 mg, 3.03 mmol) was added dropwise to the suspension of NaH (132 mg, 5.5 mmol) in dry THF at 0° C. The reaction mixture was stirred for 1 h, under Ar atm. A solution of compound 27-2 (595 mg, 2.75 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 27-3 E-isomer (117 mg, 14.8% yield); Z-isomer (7 mg, 0.8% yield).

m/z=287.4 $[M+H]^+$.

$^1H$ NMR (300 MHZ) ($CDCl_3$) δ (ppm): 1.22 (t, J=7.4 Hz, 3H); 2.90-3.01 (m, 2H); 3.16-3.31 (m, 2H); 4.12 (q, J=7.5 Hz, 2H); 6.15-6.21 (m, 1H); 7.21-7.31 (m, 2H); 7.48 (d, J=2.3 Hz, 1H).

$^{19}F$ NMR (300 MHZ) ($CDCl_3$) δ (ppm): −57.9.

Procedure for the Synthesis of Compound 27-4 (E)-2-(6-Trifluoromethoxy-1-indanylidene)ethanol To a solution of compound 27-3 (117 mg, 0.41 mmol) in dry toluene (1 mL) under nitrogen atmosphere, a solution of 1.0 M diisobutylaluminium hydride (DIBAL-H) (0.82 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 27-4 (91 mg, 91.1% yield).

m/z=191.6 $[M+H]^+$.

$^1H$ NMR (300 MHZ) ($CDCl_3$) δ (ppm): 2.02 (bs, 1H); 2.71-2.88 (m, 2H); 2.93-3.07 (m, 2H); 4.35 (d, J=7.6 Hz, 2H); 6.03-6.18 (m, 1H); 7.18-7.33 (m, 2H); 7.46 (d, J=1.9 Hz, 1H).

$^{19}F$ NMR (300 MHZ) ($CDCl_3$) δ (ppm): −57.8.

Procedure for the Synthesis of Compound 27-5 (E)-(6-Trifluoromethoxy-1-indanylidene)acetaldehyde A solution of alcohol 27-4 (91 mg, 0.373 mmol) and $MnO_2$ (324.3 mg, 3.73 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 27-5 (86 mg, 95.3% yield).

m/z=243.1 $[M+H]^+$.

$^1H$ NMR (300 MHZ) ($CDCl_3$) δ (ppm): 2.94-3.05 (m, 2H); 3.12-3.25 (m, 2H); 6.23-6.37 (m, 1H); 7.02-7.15 (m, 1H); 7.17-7.32 (m, 1H); 7.45 (bs, 1H); 9.88 (d, J=7.3 Hz, 1H).

$^{19}F$ NMR (300 MHZ) ($CDCl_3$) δ (ppm): −57.9.

Procedure for the Synthesis of Compound 27 1-[(E)-2-(6-Trifluoromethoxy-1-indanylidene)ethyl]azetidine To the solution of compound 27-5 (86 mg, 0.36 mmol) in DCE was added azetidine (22.3 mg, 0.39 mmol) with a few drops of acetic acid. The reaction mixture was stirred at room temperature for 1 h. Then, $Na(OAc)_3BH$ (152.6 mg, 0.72 mmol) was added and the reaction mixture was stirred at room temperature for overnight. The crude was extracted with EtOAc, organic layer was dried over $Na_2SO_4$, filtered and concentrated. The crude was purified by column chromatography using DCM:MeOH as eluent to give the desired product 27 (8 mg, 91% yield).

m/z=284.4 $[M+H]^+$.

$^1H$ NMR (300 MHZ) (MeOD) δ (ppm): 2.48-2.69 (m, 2H); 2.93-3.01 (m, 2H); 3.05-3.16 (m, 2H); 4.01 (d, J=8.2 Hz, 2H); 4.15-4.25 (m, 4H); 5.93-6.03 (m, 1H); 7.21 (d, J=7.7 Hz, 1H); 7.39-7.44 (m, 1H); 7.48 (bs, 1H).

$^{19}F$ NMR (300 MHZ) ($CDCl_3$) δ (ppm): −59.6.

Example 8: Compound 28-1-[(E)-2-(4-Aza-3-indanylidene)ethyl]azetidine

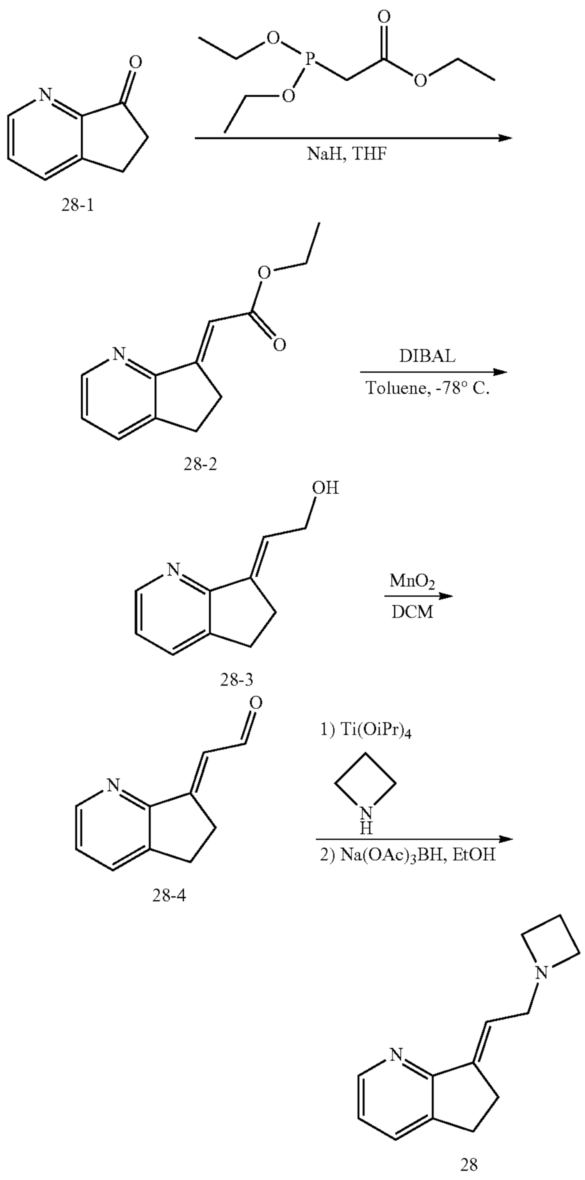

Procedure for the Synthesis of Compound 28-2 Ethyl-(E)-(4-aza-3-indanylidene)acetate Triethyl phosphonoacetate (1.82 g, 8.26 mmol) was added dropwise to the suspension of NaH (360.5 mg, 15 mmol) in dry THF at 0° C. The reaction mixture was stirred for 1 h, under Ar atm. A solution of compound 28-1 (1 g, 7.51 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 28-2 E-isomer (411 mg, 26.8% yield); Z-isomer (384 mg, 25.1% yield).

m/z=204.1 $[M+H]^+$.

$^1$H NMR (300 MHZ) ($CDCl_3$) δ (ppm): 1.36 (t, J=7.2 Hz, 3H); 3.03-3.14 (m, 2H); 3.29-3.40 (m, 2H); 4.28 (q, J=7.1 Hz, 2H); 6.84 (t, J=2.9 Hz, 1H); 7.19-7.30 (m, 1H); 7.69 (d, J=7.9 Hz, 1H); 8.54 (d, J=4.9 Hz, 1H).

Procedure for the Synthesis of Compound 28-3 (E)-2-(4-Aza-3-indanylidene)ethanol To a solution of compound 28-2 (411 mg, 2.01 mmol) in dry toluene (1 mL) under nitrogen atmosphere, a solution of 1.0 M diisobutylaluminium hydride (DIBAL-H) (4 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 28-3 (white solid, 301 mg, 92.3% yield).

m/z=162.6 $[M+H]^+$.

$^1$H NMR (300 MHZ) ($CDCl_3$) δ (ppm): 1.95 (bs, 1H); 2.91-3.06 (m, 2H); 3.07-3.25 (m, 2H); 4.55 (d, J=5.6 Hz, 2H); 6.17-6.28 (m, 1H); 7.15-7.32 (m, 1H); 7.75 (d, J=7.8 Hz, 1H); 8.54 (d, J=4.9 Hz, 1H).

Procedure for the Synthesis of Compound 28-4 (E)-(4-Aza-3-indanylidene)acetaldehyde A solution of alcohol 28-3 (300 mg, 1.86 mmol) and $MnO_2$ (1.6 g, 18.6 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 28-4 (94 mg, 31.7% yield) and unreacted starting material recovered.

m/z=160.7 $[M+H]^+$.

$^1$H NMR (300 MHZ) ($CDCl_3$) δ (ppm): 2.96-3.05 (m, 2H); 3.06-3.13 (m, 2H); 6.14-6.21 (m, 1H); 7.19-7.31 (m, 1H); 7.66 (d, J=7.8 Hz, 1H); 8.56 (d, J=4.8 Hz, 1H); 11.27 (d, J=8.3 Hz, 1H).

Procedure for the Synthesis of Compound 28 1-[(E)-2-(4-Aza-3-indanylidene)ethyl]azetidine To the solution of compound 28-4 (94 mg, 0.59 mmol) was added $Ti(OiPr)_4$ (0.27 ml, 0.89 mmol). The reaction mixture was stirred at room temperature for 1 h. Then, added azetidine (37.1 mg, 0.65 mmol) and the reaction was stirred at rt for overnight. EtOH (2 ml) and $Na(OAc)_3BH$ (250.6 mg, 1.2 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 28 (4 mg, 3.4% yield).

m/z=201.6 $[M+H]^+$.

$^1$H NMR (300 MHZ) ($CDCl_3$) δ (ppm): 2.07-2.26 (m, 2H); 2.72-2.88 (m, 2H); 2.92-3.05 (m, 2H); 3.34 (d, J=7.6 Hz, 2H); 3.45 (t, J=7.3 Hz, 4H); 6.35-6.49 (m, 1H); 7.01-7.11 (m, 1H); 7.54 (d, J=8.1 Hz, 1H); 8.41 (d, J=4.6 Hz, 1H).

Example 8: Compound 29-1-[(E)-(1-Indanylidene) methyl]propylamine

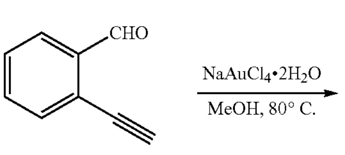

29-1

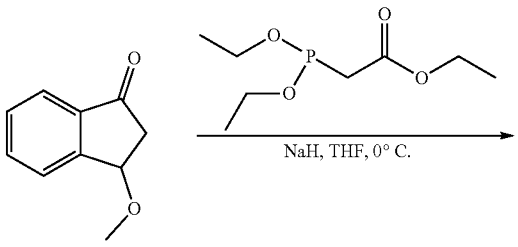

29-2

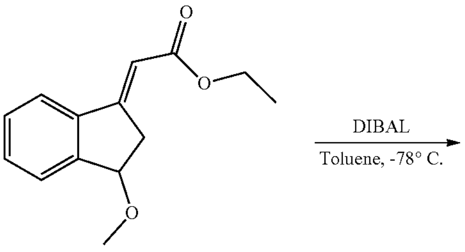

29-3

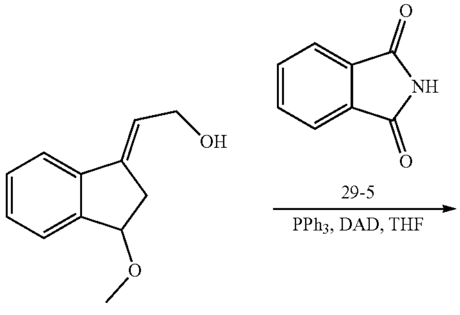

29-4

-continued

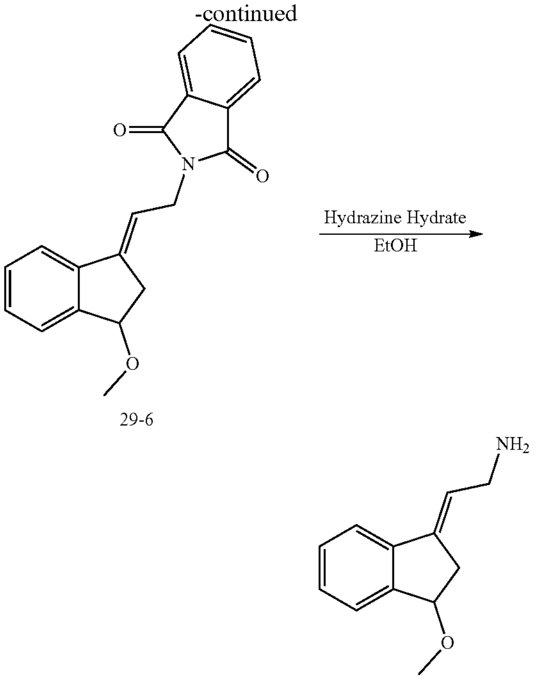

29-6

29

Procedure for the Synthesis of Compound 29-2 3-Methoxy-1-indanone

In a flame dried RBF was taken $NaAuCl_4.2H_2O$ (122.3 mg, 0.31 mmol) dissolved in MeOH at 80° C. Then, added a solution of compound 29-1 (2 g, 15.37 mmol) dissolved in MeOH slowly and the mixture was stirred at 80° C. for 5-10 minutes. The reaction mixture was cooled down to rt and the solvent was evaporated. The crude was purified by column chromatography using Hex:EtOAc as eluent to give desired product 29-2 (862 mg, 34.5% yield).

m/z=163.8 $[M+H]^+$.

$^1H$ NMR (300 MHz) ($CDCl_3$) δ (ppm): 2.55-2.64 (m, 2H); 2.88-2.99 (m, 2H); 3.44 (s, 3H); 4.93-5.00 (m, 1H); 7.38-7.50 (m, 1H); 7.57-7.66 (m, 2H); 7.70 (d, J=7.6 Hz, 1H).

Procedure for the Synthesis of Compound 29-3 Ethyl-(E)-(3-methoxy-1-indanylidene)acetate Triethyl phosphonoacetate (1.43 mg, 6.41 mmol) was added dropwise to the suspension of NaH (255.2 mg, 10.63 mmol) in dry THF at 0° C. The reaction mixture was stirred for 1 h, under Ar atm. A solution of compound 29-2 (892 mg, 5.32 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 29-3 E-isomer (304 mg, 24.7% yield); Z-isomer (20 mg, 1.6% yield).

m/z=255.8 $[M+Na]^+$.

$^1H$ NMR (300 MHZ) ($CDCl_3$) δ (ppm): 1.16 (t, J=7.2 Hz, 3H); 2.99-3.07 (m, 1H); 3.27 (m, 3H); 3.37-3.49 (m, 1H); 4.06 (q, J=7.1 Hz, 2H); 4.74-4.86 (m, 1H); 6.16 (t, J=2.5 Hz, 1H); 7.15-7.29 (m, 2H); 7.33-7.46 (m, 2H).

Procedure for the Synthesis of Compound 29-4 (E)-2-(3-Methoxy-1-indanylidene)ethanol To a solution of compound 29-3 (304 mg, 1.31 mmol) in dry toluene (1 mL) under nitrogen atmosphere, a solution of 1.0 M diisobutylaluminium hydride (DIBAL-H) (2.6 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 29-4 (235 mg, 94.4% yield).

m/z=213.8 $[M+Na]^+$.

$^1H$ NMR (300 MHZ) ($CDCl_3$) δ (ppm): 2.03 (bs, 1H); 2.59-2.73 (m, 1H); 2.91-3.03 (m, 1H); 3.36 (s, 3H); 4.27 (d, J=7.4 Hz, 2H); 4.81-4.88 (m, 1H); 6.04-6.14 (m, 1H); 7.18-7.29 (m, 2H); 7.34-7.49 (m, 2H).

Procedure for the Synthesis of Compound 29-6 (2-[(E)-2-(3-Methoxy-1-indanylidene)ethyl]-2H-isoindole-1,3-dione To the solution of compound 29-4 (104 mg, 0.55 mmol), diisopropyl azodicarboxylate (DIAD) (0.13 ml, 0.66 mmol) and compound 29-5 (96.52 mg, 0.66 mmol) in dry THF at 0° C. was added triphenylphosphine ($PPh_3$) (173 mg, 0.66 mmol). The reaction mixture was stirred for at 50° C. for overnight and then quenched with water. The crude was extracted with EtOAc, organic layer was dried over $Na_2SO_4$, filtered and concentrated. The crude was purified by column chromatography using Hex:EtOAc as eluent to give the desired product 29-6 (122 mg, 70.1% yield).

m/z=320.9 $[M+H]^+$.

$^1H$ NMR (300 MHZ) ($CDCl_3$) δ (ppm): 2.88-3.05 (m, 1H); 3.25-3.38 (m, 1H); 3.44 (s, 3H); 4.45 (d, J=8.1 Hz, 2H); 4.92-5.02 (m, 1H); 5.98-6.16 (m, 1H); 7.13-7.94 (m, 9H).

Procedure for the Synthesis of Compound 29 (1-[(E)-(1-Indanylidene)methyl]propylamine To the solution of compound 29-6 (120 mg, 0.37 mmol) in EtOH was added hydrazine monohydrate (0.036 ml, 0.75 mmol). The reaction mixture was stirred for at rt for 2-3 hours. Solvent was evaporated and the crude was purified by column chromatography using DCM:MeOH as eluent to give the desired product 29 (55 mg, 77.4% yield).

m/z=212.8 $[M+Na]^+$.

$^1H$ NMR (300 MHZ) (MeOD) δ (ppm): 2.62-2.81 (m, 1H); 2.89-3.07 (m, 1H); 3.34 (s, 3H); 3.58-3.83 (m, 2H); 4.77-4.83 (m, 2H); 6.02-6.20 (m, 1H); 7.13-7.24 (m, 2H); 7.36 (d, J=7.5 Hz, 1H); 7.46 (d, J=7.2 Hz, 1H).

Example 9: Compound 30-1-[(E)-2-(3-Methoxy-1-indanylidene)ethyl]azetidine

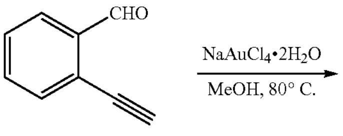

30-1

-continued

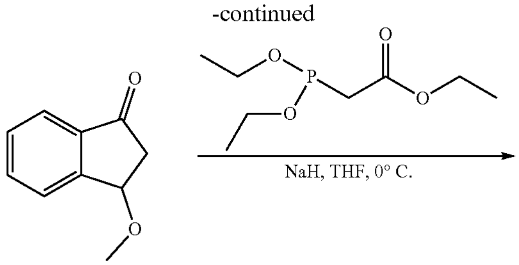

30-2

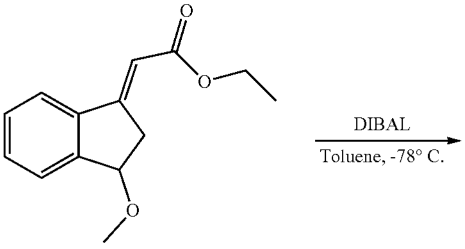

30-3

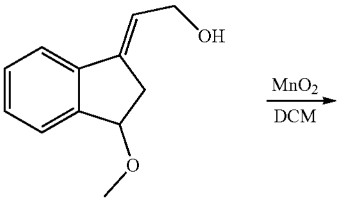

30-4

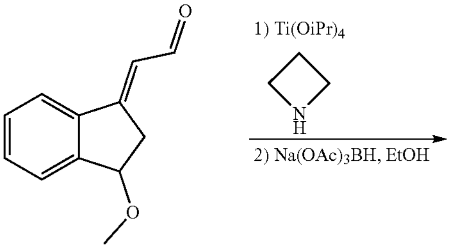

30-5

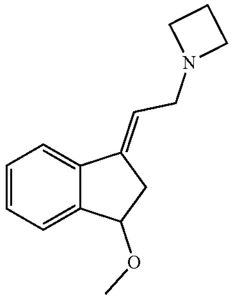

30

Similar synthetic procedure as for compound 29 synthesis.

Procedure for the Synthesis of Compound 30 1-[(E)-2-(3-Methoxy-1-indanylidene)ethyl]azetidine To the solution of compound 30-5 (220 mg, 1.17 mmol) was added $Ti(OiPr)_4$ (0.53 ml, 1.76 mmol). The reaction mixture was stirred at room temperature for 1 h. Then, added azetidine (73.4 mg, 1.3 mmol) and the reaction was stirred at rt for overnight. EtOH (2 ml) and $Na(OAc)_3BH$ (496.1 mg, 2.3 mmol) were added to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 30 (10 mg, 3.7% yield). m/z=230.2 $[M+H]^+$. $^1H$ NMR (300 MHZ) ($CDCl_3$) δ (ppm): 2.04-2.20 (m, 2H); 2.63-2.75 (m, 1H); 2.92-3.15 (m, 1H); 3.16-3.34 (m, 6H); 3.40 (s, 3H); 4.82-4.98 (m, 1H); 5.88-6.05 (m, 1H); 7.19-7.33 (m, 2H); 7.38-7.52 (m, 2H).

Example 10: Compound 31—N,N-Dimethyl[(E)-2-{2-thiabicyclo[3.3.0]octa-1(5),3-dien-6-ylidene}ethyl]amine

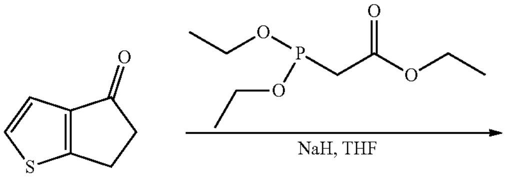

31-1

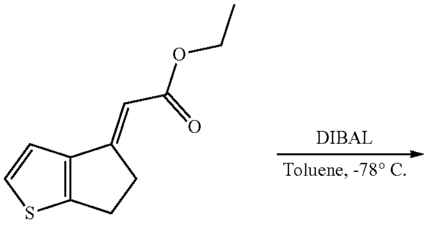

31-2

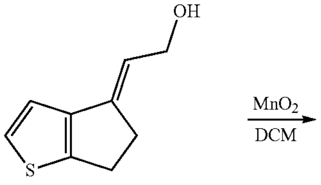

31-3

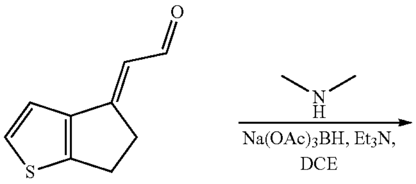

31-4

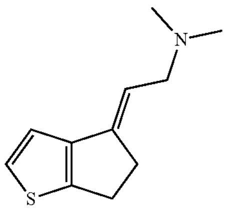

31

Procedure for the Synthesis of Compound 31-2 Ethyl-(E)-{2-thiabicyclo[3.3.0]octa-1(5),3-dien-6-ylidene}acetate Triethyl phosphonoacetate (1.95 g, 8.68 mmol) was added dropwise to the suspension of NaH (579.2 mg, 24.13 mmol)

in dry THF at 0° C. The reaction mixture was stirred for 1 h, under Ar atm. A solution of compound 31-1 (1 g, 7.24 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 31-2 E-isomer (250 mg, 16.6% yield); Z-isomer (35 mg, 2.3% yield).

m/z=209.7 $[M+H]^+$.

$^1$H NMR (300 MHZ) ($CDCl_3$) δ (ppm): 1.54 (t, J=7.41 Hz, 3H); 3.27-3.36 (m, 2H); 3.80-3.91 (m, 2H); 4.03 (s, 3H); 4.44 (q, J=6.99 Hz, 2H); 6.18 (t, J=2.4 Hz, 1H); 7.25 (d, J=5.3 Hz, 1H); 7.49 (d, J=5.3 Hz, 1H).

Procedure for the Synthesis of Compound 31-3 (E)-2-{2-Thiabicyclo[3.3.0]octa-1(5),3-dien-6-ylidene}ethanol To a solution of compound 31-2 (219 mg, 1.05 mmol) in dry toluene (1 mL) under nitrogen atmosphere, a solution of 1.0 M diisobutylaluminium hydride (DIBAL-H) (2.1 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 31-3 (150 mg, 85.8% yield).

m/z=167.8 $[M+H]^+$.

$^1$H NMR (300 MHZ) ($CDCl_3$) δ (ppm): 1.97 (bs, 1H); 3.24-3.36 (m, 2H); 3.38-3.54 (m, 2H); 4.56 (d, J=7.04 Hz, 2H); 5.97-6.09 (m, 1H); 7.25 (d, J=5.2 Hz, 1H); 7.50 (d, J=5.3 Hz, 1H).

Procedure for the Synthesis of Compound 31-4 (E)-{2-Thiabicyclo[3.3.0]octa-1(5),3-dien-6-ylidene}acetaldehyde A solution of alcohol 31-3 (30 mg, 0.18 mmol) and $MnO_2$ (78.44 mg, 0.9 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 31-4 (10 mg, 33.7% yield).

m/z=165.7 $[M+H]^+$.

$^1$H NMR (300 MHZ) ($CDCl_3$) δ (ppm): 3.15-3.33 (m, 2H); 3.56-3.68 (m, 2H); 6.14-6.20 (m, 1H); 7.01 (d, J=5.2 Hz, 1H); 7.32 (d, J=5.3 Hz, 1H); 9.92 (d, J=7.6 Hz, 1H).

Procedure for the Synthesis of Compound 31 N,N-Dimethyl[(E)-2-{2-thiabicyclo[3.3.0]octa-1(5),3-dien-6-ylidene}ethyl]amine To the solution of compound 31-4 (50 mg, 0.30 mmol) in DCE was added dimethylamine hydrochloride (27.2 mg, 0.34 mmol), along with $Et_3N$ (0.075 ml, 0.34 mmol). The reaction mixture was stirred at room temperature for 1 h. Then, $Na(OAc)_3BH$ (70.9 mg, 0.53 mmol) was added and the reaction mixture was stirred at room temperature for overnight. The crude was extracted with EtOAc, organic layer was dried over $Na_2SO_4$, filtered and concentrated. The crude was purified by column chromatography using DCM: MeOH as eluent to give the desired product 31 (5 mg, 8.5% yield).

m/z=194.9 $[M+H]^+$.

$^1$H NMR (300 MHZ) ($CDCl_3$) δ (ppm): 2.75 (s, 6H); 3.05-3.11 (m, 2H); 3.112-3.23 (m, 2H); 3.66 (d, J=7.9 Hz, 2H); 5.63-5.73 (m, 1H); 7.02 (d, J=4.94 Hz, 1H); 7.23 (d, J=5.3 Hz, 1H).

Example 11: Compound 32—(E) N,N-Dimethyl [(E)-2-(6-isopropoxy-1-indanylidene)ethyl]amine

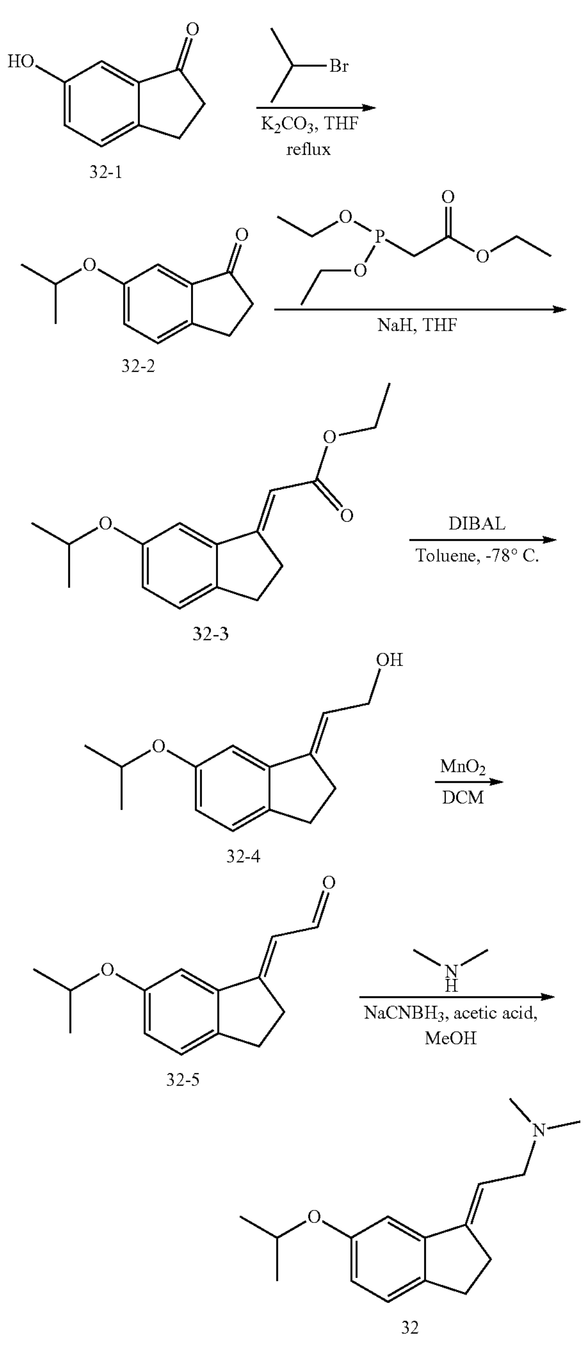

Procedure for the Synthesis of Compound 32-2 6-Isopropoxy-1-indanone

To a flame dried RBF was taken compound 32-1 (2 g, 13.5 mmol) dissolved in DMF. $Cs_2CO_3$ (8.8 g, 26.8 mmol) was added to the reaction mixture, followed by the addition of 2-bromopropane (2.5 ml, 26.8 mmol). The suspension was stirred at 60° C. for overnight. Solvent was evaporated and the crude was extracted with EtOAc. Organic layer was dried over $Na_2SO_4$, filtered, and concentrated. The crude was purified by column chromatography using Hex:EtOAc as eluent to give desired product 32-2 (1.6 g, 61.5% yield).

m/z=191.7 $[M+H]^+$.

$^1$H NMR (300 MHZ) ($CDCl_3$) δ (ppm): 1.41 (s, 3H); 1.42 (s, 3H); 2.73-2.83 (m, 2H); 3.09-3.19 (m, 2H); 4.59-4.75 (m, 1H); 7.19-7.28 (m, 2H); 7.43 (d, J=9.3 Hz, 1H).

Procedure for the Synthesis of Compound 32-3 Ethyl-(E)-(6-isopropoxy-1-indanylidene)acetate Triethyl phosphonoacetate (2.6 g, 11.6 mmol) was added dropwise to the suspension of NaH (504 mg, 21 mmol) in dry THF at 0° C. The reaction mixture was stirred for 1 h, under Ar atm. A solution of compound 32-2 (2 g, 10.5 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 32-3 (1.0 g, 36.6% yield); Z-isomer (200 mg, 7.3% yield).

m/z=261.6 $[M+H]^+$.

$^1$H NMR (300 MHZ) ($CDCl_3$) δ (ppm): 1.54 (s, 3H); 1.55 (s, 3H); 3.12-3.25 (m, 2H); 3.42-3.53 (m, 2H); 4.66-4.88 (m, 1H); 6.44 (t, J=2.6 Hz, 1H); 6.93-6.98 (m, 1H); 7.26 (d, J=2.7 Hz, 1H); 7.50 (d, J=7.5 Hz, 1H).

Procedure for the Synthesis of Compound 32-4 (E)-2-(6-Isopropoxy-1-indanylidene)ethanol To a solution of compound 32-3 (1.4 g, 5.4 mmol) in dry toluene (1 mL) under nitrogen atmosphere, a solution of 1.0 M diisobutylaluminium hydride (DIBAL-H) (10.7 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 32-4 (white solid, 1.1 g, 94% yield).

m/z=219.6 $[M+H]^+$.

$^1$H NMR (300 MHZ) ($CDCl_3$) δ (ppm): 1.32 (s, 3H); 1.34 (s, 3H); 1.52 (bs, 1H); 2.74-2.84 (m, 2H); 2.87-2.96 (m, 2H); 4.34 (d, J=6.6 Hz, 2H); 4.48-4.61 (m, 1H); 5.98-6.11 (m, 1H); 6.93-6.98 (m, 1H); 7.26 (d, J=2.7 Hz, 1H); 7.50 (d, J=7.5 Hz, 1H).

Procedure for the Synthesis of Compound 32-5 (E)-(6-Isopropoxy-1-indanylidene)acetaldehyde A solution of alcohol 32-4 (1.2 g, 5.5 mmol) and $MnO_2$ (4.8 g, 55 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 32-5 (300 mg, 25% yield).

m/z=217.7 $[M+H]^+$.

$^1$H NMR (300 MHZ) ($CDCl_3$) δ (ppm): 1.52 (s, 3H); 1.54 (s, 3H); 3.21-3.32 (m, 2H); 3.43-3.54 (m, 2H); 4.67-4.80 (m, 1H); 6.57-6.66 (m, 1H); 7.13-7.21 (m, 1H); 7.26 (d, J=2.4 Hz, 1H); 7.46 (d, J=2.4 Hz, 1H); 10.24 (d, J=7.9 Hz, 1H).

Procedure for the Synthesis of Compound 32 (E) N,N-Dimethyl[(E)-2-(6-isopropoxy-1-indanylidene)ethyl]amine To a mixture of compound 32-5 (114 mg, 0.53 mmol) and dimethylamine (26.1 mg, 0.58 mmol) was added a few drops of acetic acid. The reaction mixture was stirred at room temperature for 3 hours. Then, added $NaCNBH_3$ (46.6 mg, 0.74 mmol) to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 32 (yellow oil, 2 mg).

m/z=246.7 $[M+H]^+$.

$^1$H NMR (300 MHZ) ($CDCl_3$) δ (ppm): 1.31 (s, 3H); 1.33 (s, 3H); 2.43 (s, 6H); 2.71-2.81 (m, 2H); 2.89-2.99 (m, 2H); 3.26 (d, J=7.7 Hz, 2H); 4.44-4.61 (m, 1H); 5.90-6.02 (m, 1H); 6.75-6.82 (m, 1H); 6.99 (d, J=2.4 Hz, 1H); 7.131 (d, J=8.4 Hz, 1H).

Example 12: Compound 33-(E)[(E)-2-(6-Methoxy-1-indanylidene)ethyl]-N-methyl(isopropyl)amine

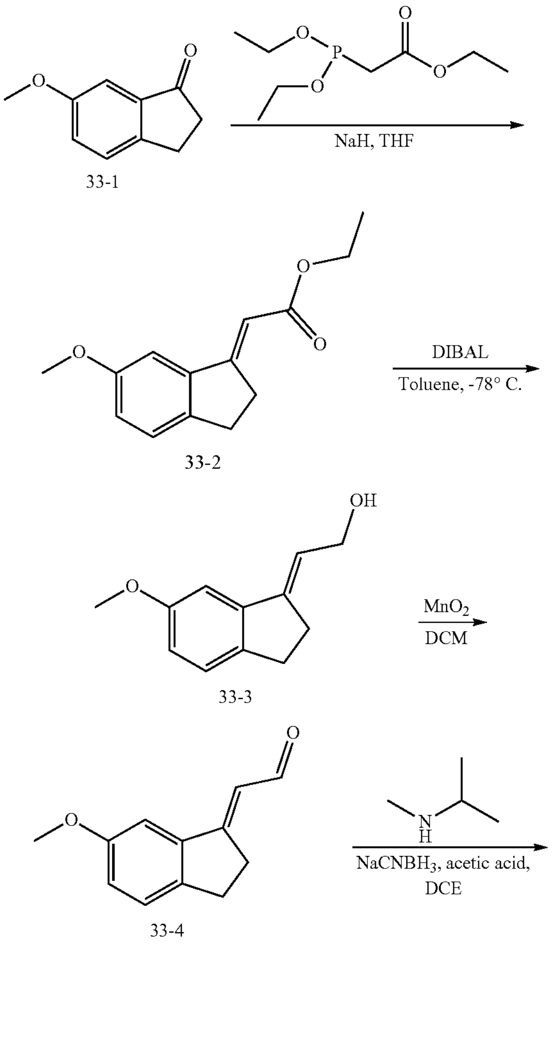

-continued

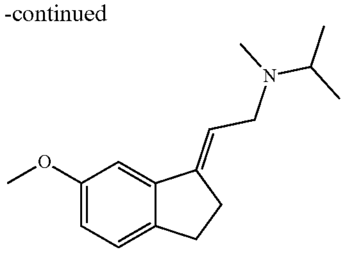

33

Procedure for the Synthesis of Compound 33-2 Ethyl-(E)-(6-methoxy-1-indanylidene)acetate Triethyl phosphonoacetate (3.3 g, 14.8 mmol) was added dropwise to the suspension of NaH (592 mg, 24.7 mmol) in dry THF at 0° C. The reaction mixture was stirred for 1 h, under Ar atm. A solution of compound 33-1 (2 g, 12.33 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex: EtOAc as eluent to give desired product 33-2 E-isomer (1.5 mg, 52.4% yield); Z-isomer (110 mg, 3.5% yield).

m/z=233.7 $[M+H]^+$.

$^1H$ NMR (300 MHZ) ($CDCl_3$) δ (ppm): 1.54 (t, J=7.1 Hz, 3H); 3.15-3.26 (m, 2H); 3.48-3.56 (m, 2H); 4.03 (s, 3H); 4.43 (q, J=7.4 Hz, 2H); 6.47 (t, J=2.5 Hz, 1H); 7.12-7.18 (m, 1H); 7.26 (d, J=2.6 Hz, 1H); 7.42-7.47 (m, 1H).

Procedure for the Synthesis of Compound 33-3 (E)-2-(6-Methoxy-1-indanylidene)ethanol To a solution of compound 33-2 (1.5 g, 6.5 mmol) in dry toluene (1 mL) under nitrogen atmosphere, a solution of 1.0 M diisobutylaluminium hydride (DIBAL-H) (13 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 33-3 (white solid, 1.1 g, 91.6% yield).

m/z=191.6 $[M+H]^+$.

$^1H$ NMR (300 MHZ) ($CDCl_3$) δ (ppm): 1.86 (bs, 1H); 2.99-3.15 (m, 2H); 3.16-3.28 (m, 2H); 4.09 (s, 3H); 4.63 (d, J=7.6 Hz, 2H); 6.27-6.41 (m, 1H); 7.05-7.11 (m, 1H); 7.27 (d, J=2.4 Hz, 1H); 7.42 (d, J=8.6 Hz, 1H).

Procedure for the Synthesis of Compound 33-4 (E)-(6-Methoxy-1-indanylidene)acetaldehyde A solution of alcohol 33-3 (1.1 g, 5.8 mmol) and $MnO_2$ (5.04 g, 58 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 33-4 (573 mg, 53% yield).

m/z=189.7 $[M+H]^+$.

$^1H$ NMR (300 MHZ) ($CDCl_3$) δ (ppm): 3.22-3.32 (m, 2H); 3.40-3.60 (m, 2H); 4.02 (s, 3H); 6.60-6.82 (m, 1H); 7.13-7.31 (m, 2H); 7.46 (d, J=8.3 Hz, 1H); 10.24 (d, J=7.3 Hz, 1H).

Procedure for the Synthesis of Compound 33 (E) [(E)-2-(6-Methoxy-1-indanylidene)ethyl]-N-methyl (isopropyl)amine To a mixture of compound 33-4 (159 mg, 0.845 mmol) and N-isopropylmethylamine (68 mg, 0.93 mmol) was added a few drops of acetic acid. The reaction mixture was stirred at room temperature for 3 hours. Then, added $NaCNBH_3$ (74.3 mg, 1.2 mmol) to the reaction mixture and was stirred at room temperature for 2-3 hours. The crude was extracted with EtOAc, organic layer was dried over $Na_2SO_4$, filtered and concentrated. The crude was purified by column chromatography using DCM:MeOH as eluent to give the desired product 33 (yellow oil, 5 mg).

m/z=246.6 $[M+H]^+$.

$^1H$ NMR (300 MHZ) ($CDCl_3$) δ (ppm): 1.06 (s, 3H); 1.08 (s, 3H); 2.25 (s, 3H); 2.69-2.80 (m, 2H); 2.85-2.99 (m, 3H); 3.23 (d, J=8.2 Hz, 2H); 3.79 (s, 3H); 6.73-6.79 (m, 1H); 6.98 (d, J=2.4 Hz, 2H); 7.11 (d, J=8.6 Hz, 1H).

Example 13: Compound 101-1-[(E)-(1-Indanylidene)methyl]propylamine

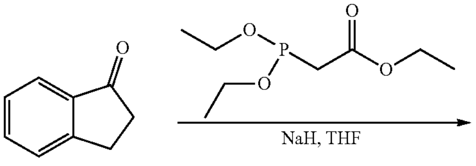

101-1

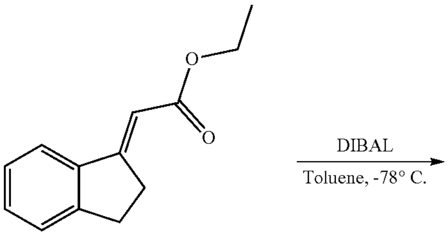

101-2

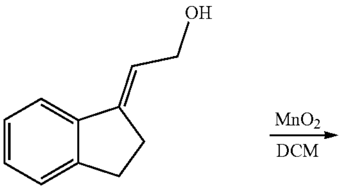

101-3

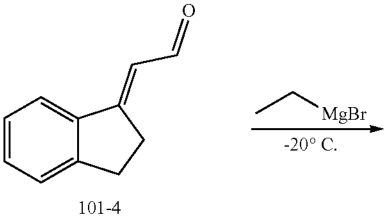

101-4

-continued

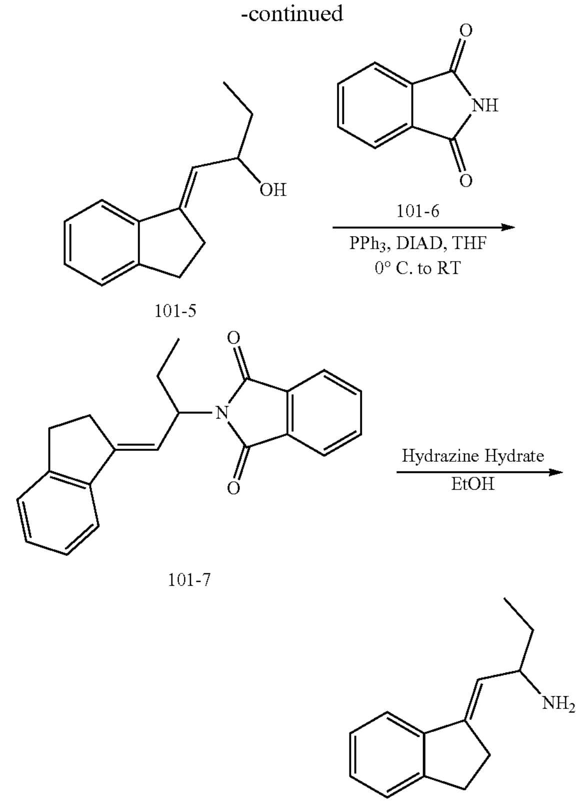

101-5

101-6

101-7

101

Procedure for the Synthesis of Compound 101-2 Ethyl-(E)-(1-indanylidene)acetate

Triethyl phosphonoacetate (5.1 ml, 22.7 mmol) was added dropwise to the suspension of NaH (1.2 g, 2 eq) in dry THF at 0° C. The reaction mixture was stirred for 1 h, under Ar atm. A solution of compound 101-1 (2 g, 15.13 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by column chromatography using Hex:EtOAc as eluent to give desired product 101-2 E-isomer (102 mg, 33.3% yield); Z-isomer (97 mg, 31.6% yield).

m/z=203.7 $[M+H]^+$.

$^1$H NMR (300 MHZ) ($CDCl_3$) δ (ppm): 1.24 (t, J=7.2 Hz, 3H); 2.94-3.04 (m, 2H); 3.17-3.25 (m, 2H); 4.14 (q, J=6.99 Hz, 2H); 6.23 (t, J=2.3 Hz, 1H); 7.12-7.19 (m, 1H); 7.25 (d, J=3.7 Hz, 1H); 7.52 (d, J=8.1 Hz, 1H).

Procedure for the Synthesis of Compound 101-3 (E)-2-(1-Indanylidene)ethanol

To a solution of compound 101-2 (102 mg, 0.51 mmol) in dry toluene (1 mL) under nitrogen atmosphere, a solution of 1.0 M diisobutylaluminium hydride (DIBAL-H) (1 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 101-3 (18 mg, 21.1% yield).

m/z=161.6 $[M+H]^+$.

$^1$H NMR (300 MHZ) ($CDCl_3$) δ (ppm): 1.65 (bs, 1H); 2.75-2.90 (m, 2H); 2.99-3.11 (m, 2H); 4.40 (d, J=6.7 Hz, 2H); 6.11-6.22 (m, 1H); 7.22-7.34 (m, 3H); 7.47-7.57 (m, 1H).

Procedure for the Synthesis of Compound 101-4 (E)-(1-Indanylidene)acetaldehyde

A solution of alcohol 101-3 (65 mg, 0.41 mmol) and $MnO_2$ (176.4 mg, 2.03 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 101-4 (59 mg, 91.9% yield).

m/z=159.7 $[M+H]^+$.

$^1$H NMR (300 MHZ) ($CDCl_3$) δ (ppm): 2.93-3.09 (m, 2H); 3.11-3.26 (m, 2H); 6.34-6.41 (m, 1H); 7.17-7.29 (m, 4H); 7.51 (d, J=7.6 Hz, 1H); 9.92 (d, J=7.8 Hz, 1H).

Procedure for the Synthesis of Compound 101-5 (E)-1-(1-Indanylidene)-2-butanol

To the solution of compound 101-4 (21 mg, 0.13 mmol) in dry THF at 0° C. Then added EtMgBr (1.0 M, 0.16 ml, 2 eq) dropwise to the reaction mixture. The reaction mixture was stirred for 1 hour at rt and then quenched with $NH_4Cl$ solution. The crude was extracted with EtOAc, organic layer was dried over $Na_2SO_4$, filtered and concentrated. The crude was purified by column chromatography using Hex:EtOAc as eluent to give the desired product 101-5 (20 mg, 80.3% yield).

m/z=189.8 $[M+H]^+$.

$^1$H NMR (300 MHZ) ($CDCl_3$) δ (ppm): 1.01 (t, J=7.4 Hz, 3H); 1.54-1.90 (m, 2H); 2.71-2.97 (m, 2H); 3.04 (d, J=7.1 Hz, 2H); 4.37-4.50 (m, 1H); 7.15-7.34 (m, 3H); 7.48-7.56 (m, 1H).

Procedure for the Synthesis of Compound 101-7 (2-{1-[(E)-(1-Indanylidene)methyl]propyl}-2H-isoindole-1,3-dione To the solution of compound 101-5 (100 mg, 0.53 mmol), DIAD (0.125 ml, 0.64 mmol) and compound 101-6 (93.8 mg, 0.64 mmol) in dry THF at 0° C. was added PPh3 (167 mg, 0.64 mmol). The reaction mixture was stirred for at 50° C. for overnight and then quenched with water. The crude was extracted with EtOAc, organic layer was dried over $Na_2SO_4$, filtered and concentrated. The crude was purified by column chromatography using Hex:EtOAc as eluent to give the desired product 101-7 (24 mg, 14.2% yield).

m/z=318.8 $[M+H]^+$.

$^1$H NMR (300 MHZ) ($CDCl_3$) δ (ppm): 1.02 (t, J=7.4 Hz, 3H); 2.06-2.27 (m, 2H); 2.84-2.97 (m, 2H); 3.00-3.11 (m, 2H); 4.37-4.50 (m, 1H); 6.43-6.51 (m, 1H); 7.21-7.34 (m, 4H); 7.68-7.80 (m, 2H); 7.84-7.94 (m, 2H).

Procedure for the Synthesis of Compound 101 (1-[(E)-(1-Indanylidene)methyl]propylamine To the solution of compound 7 (26 mg, 0.08 mmol) in EtOH was added hydrazine monohydrate (0.005 ml, 0.09 mmol). The reaction mixture was stirred for at rt for 2-3 hours. Solvent was evaporated and the crude was purified by column chromatography using DCM:MeOH as eluent to give the desired product 101 (5 mg, 32% yield).

m/z=187.8 $[M+H]^+$.

$^1$H NMR (300 MHZ) (MeOD) δ (ppm): 0.89 (t, J=7.8 Hz, 3H); 1.54-1.73 (m, 1H); 1.75-1.91 (m, 1H); 2.59-2.87 (m, 2H); 2.89-2.97 (m, 2H); 3.79-3.97 (m, 1H); 5.67-5.77 (m, 1H); 7.05-7.22 (m, 3H); 7.45 (d, J=7.9 Hz, 2H).

Example 14: Compound 102-2-[(E)-(6-Methoxy-1-indanylidene)methyl]-1-methylpyrrolidine

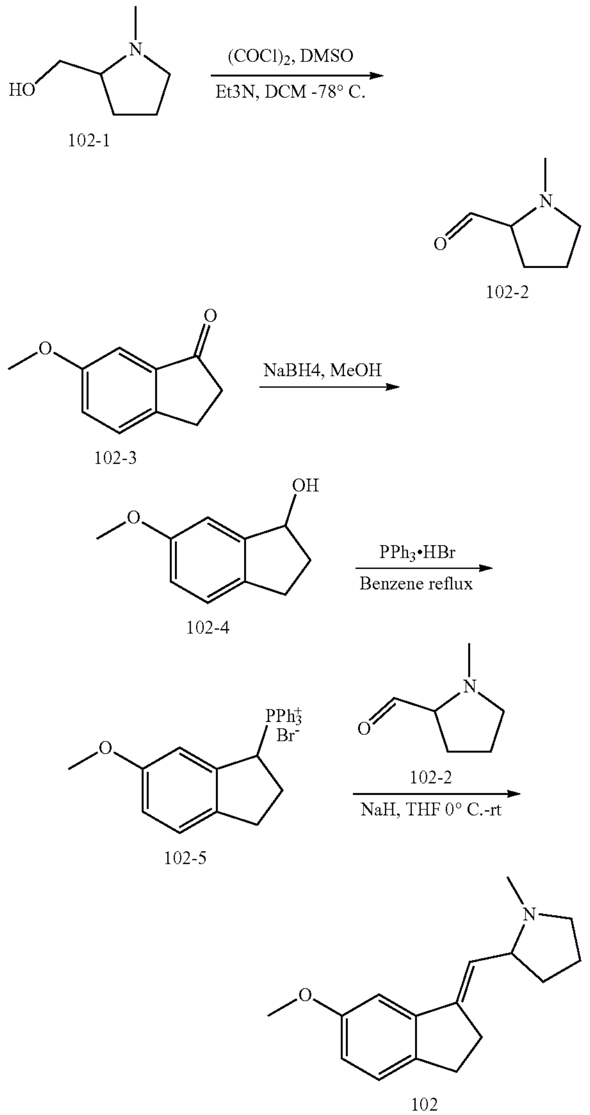

102-1

102-2

102-3

102-4

102-5

102-2

102

Procedure for the Synthesis of Compound 102-2 1-Methyl-2-pyrrolidinecarbaldehyde To a flame dried RBF was added oxalyl chloride (1.13 ml, 12.99 mmol) at −78° C. in DMC. DMSO (1.85 ml, 25.98 mmol) was added dropwise to the reaction mixture and the mixture was stirred at 30 minutes. Followed by the dropwise addition of compound 102-1 (1 g, 8.68 mmol) solution in DCM. The reaction mixture was stirred at rt for 2-3 hours, then added $Et_3N$ (8.5 ml, 60.8 mmol). The reaction mixture was stirred at rt for overnight. Quenched with sat $NaHCO_3$ solution, and extracted with EtOAc, organic layer was dried over $Na_2SO_4$, filtered and concentrated. The crude was used directly for next step 102-2 (800 mg, 82% yield).

m/z=114.6 $[M+H]^+$.

$^1$H NMR (300 MHZ) ($CDCl_3$) δ (ppm): 1.29-1.41 (m, 2H); 1.98-2.22 (m, 2H); 2.51 (s, 3H); 3.12 (t, J=7.61 Hz, 2H); 4.12-4.23 (m, 1H); 9.43 (d, J=4.1 Hz, 1H).

Procedure for the Synthesis of Compound 102-4 6-Methoxy-1-indanol $NaBH_4$ (559.8 mg, 14.8 mmol) was added to a solution of compound 102-3 (2 g, 12.33 mmol) in MeOH. The reaction mixture was stirred at rt for one hour. Quenched with water, and extracted with EtOAc, organic layer was dried over $Na_2SO_4$, filtered and concentrated. The crude was used directly for next step 102-4 (2 g, 99% yield).

m/z=165.6 $[M+H]^+$.

$^1$H NMR (300 MHZ) ($CDCl_3$) δ (ppm): 2.19 (bs, 1H); 2.21-2.33 (m, 1H); 2.73-2.87 (m, 1H); 2.95-3.14 (m, 1H); 3.19-3.36 (m, 1H); 4.11 (s, 3H); 5.51 (t, J=6.5 Hz, 1H); 7.09-7.16 (m, 1H); 7.24-7.28 (m, 1H); 7.44 (d, J=8.1 Hz, 1H).

Procedure for the Synthesis of Compound 102-5 6-Methoxy-1-indanyltriphenylphosphonium Compound 102-4 (1 g, 6.09 mmol) and triphenylphosphine ($PPh_3$). HBr (2.1 g, 6.09 mmol) were taken in a flame dried RBF dissolved in benzene. The reaction mixture was refluxed for overnight under $N_2$ atm. The precipitate was filtered off and dried. The solid was suspended in ether and stirred for 20 minutes. The phosphonium salt was filtered off and dried under vacuum. The salt was used directly for next step 102-5 (2.1 g, 99% yield).

m/z=411.6 $[M+H]^+$.

$^1$H NMR (300 MHZ) ($CDCl_3$) δ (ppm): 1.28-1.48 (m, 1H); 2.14-2.38 (m, 1H); 2.40-2.67 (m, 1H); 3.02-3.26 (m, 1H); 3.29-3.42 (m, 1H); 6.11-6.18 (m, 1H); 6.61-6.78 (m, 2H); 7.44-7.77 (m, 15H).

Procedure for the Synthesis of Compound 102 2-[(E)-(6-Methoxy-1-indanylidene)methyl]-1-methylpyrrolidine Compound 102-5 (3.1 g, 6.33 mmol) was taken in a flame dried RBF dissolved in THF at 0° C. To the suspension was added NaH (254.5 mg, 1.2 eq) and the reaction mixture was stirred for 1 h, under Ar atm. A solution of compound 102-2 (600 mg, 5.3 mmol) in dry THF (5 ml) was added dropwise to the reaction mixture. The suspension was stirred at room temperature for overnight. The reaction mixture was quenched with sat. $NH_4Cl$ solution and extracted with EtOAc. Organic layer was dried over $Na_2SO_4$, filtered, and concentrated. The crude was purified by semi-prep HPLC (3 mg).

m/z=244.6 $[M+H]^+$.

$^1$H NMR (300 MHZ) (MeOD) δ (ppm): 1.78-1.98 (m, 2H); 2.03-2.31 (m, 3H); 2.41-2.62 (m, 2H); 2.79 (s, 3H); 3.06-3.23 (m, 2H); 3.53-3.69 (m, 2H); 3.86 (s, 3H); 4.53-4.63 (m, 1H); 5.49 (d, J=8.5 Hz, 1H); 6.92-6.97 (m, 1H); 7.14-7.18 (m, 1H); 7.28 (d, J=8.5 Hz, 1H).

Example 15: Compound 103—{(E)-3-[2-(1-Azetidinyl)ethylidene]-5-indanyl}methanol

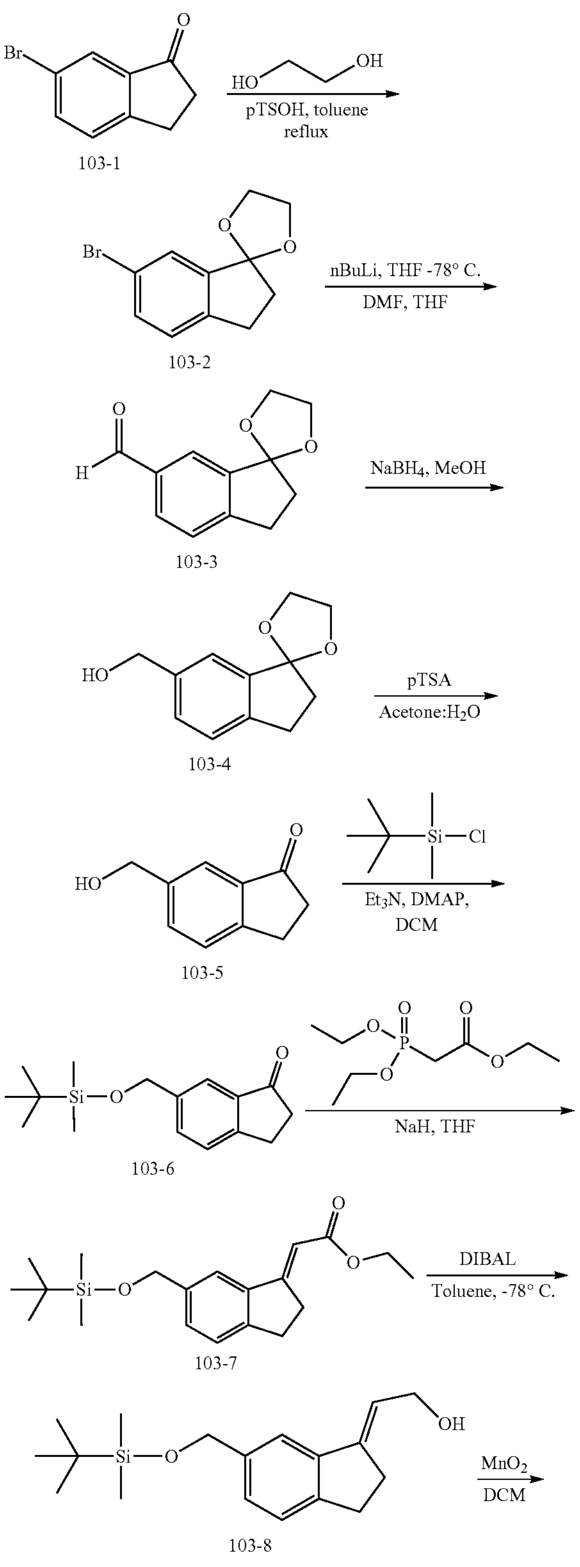

103-1
103-2
103-3
103-4
103-5
103-6
103-7
103-8

-continued

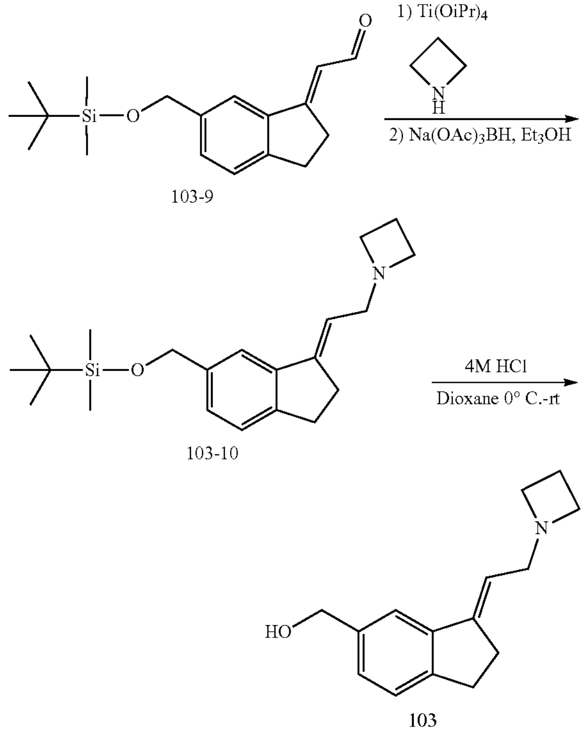

103-9
103-10
103

Procedure for the Synthesis of Compound 103-2
6'-Bromospiro[1,3-dioxolane-2,1'-indan]

To the solution of compound 103-1 (5 g, 23.7 mmol) in toluene was added compound 2 (26.4 ml, 474 mmol) and p-toluenesulfonic acid (pTSA) (0.045 g, 0.237 mmol). The reaction mixture was fitted with Dean Starks apparatus and refluxed for 2-3 hours. The suspension was cooled down to room temperature and extracted with EtOAc. Organic layer was dried over $Na_2SO_4$, filtered, and concentrated. The crude was purified by column chromatography using Hex:EtOAc as eluent to give desired product 103-2 (6 g, 99.3% yield).

m/z=255.42, 257.43.

$^1$H NMR (300 MHZ) ($CDCl_3$) δ (ppm): 2.43 (t, J=6.8 Hz, 2H); 3.03 (t, J=6.8 Hz, 2H); 4.20-4.24 (m, 2H); 4.29-4.34 (m, 2H); 7.24 (d, J=7.4 Hz, 1H); 7.53-7.58 (m, 1H); 7.59-7.63 (m, 1H).

Procedure for the Synthesis of Compound 103-3
Spiro[1,3-dioxolane-2,1'-indan]-6'-carbaldehyde To the precooled (−78° C.) solution of compound 103-2 (5 g, 23.7 mmol) in THF was slowly added nBuLi (2.5 M in Hexane, 1.1 eq). The reaction mixture was stirred at −78° C. for 20 minutes. Then, added DMF (1.82 ml, 23.5 mmol) and the resulting reaction mixture was stirred at −78° C. for 15 minutes. The reaction mixture was allowed to warm up to room temperature and stirred for another 30 minutes. Quenched with sat aq $NaHCO_3$ and diluted with EtOAc. Organic layer was dried over $Na_2SO_4$, filtered, and concentrated. The crude was purified by column chromatography using Hex:EtOAc as eluent to give desired product 103-3 (3.99 g, 99.8% yield).

m/z=227.54 (M+Na)$^+$.

$^1$H NMR (300 MHZ) ($CDCl_3$) δ (ppm): 2.21 (t, J=6.8 Hz, 2H); 2.87 (t, J=6.8 Hz, 2H); 3.93-4.00 (m, 2H); 4.03-4.13 (m, 2H); 7.24 (d, J=7.6 Hz, 1H); 7.70 (d, J=7.6 Hz, 1H); 7.73 (s, 1H); 9.85 (s, 1H).

Procedure for the Synthesis of Compound 103-4 (Spiro[1,3-dioxolane-2,1'-indan]-6'-yl)methanol57

To the solution of compound 103-3 (540 mg, 2.64 mmol) in MeOH at 0° C. was slowly added $NaBH_4$ (120 mg, 3.17 mmol). The reaction mixture was stirred at room temperature for 2-3 hours. Quenched with water and crude was extracted with EtOAc, organic layer was dried over $Na_2SO_4$, filtered, and concentrated to give desired product 103-4 (535 mg, 98.1% yield).

m/z=207.63 $(M+H)^+$.

$^1$H NMR (300 MHZ) ($CDCl_3$) δ (ppm): 2.21 (t, J=6.8 Hz, 2H); 2.51 (bs, 1H); 2.85 (t, J=6.8 Hz, 2H); 3.93-4.00 (m, 2H); 4.06-4.14 (m, 2H); 4.52 (s, 2H); 7.11 (d, J=8.5 Hz, 1H); 7.21 (d, J=8.5 Hz, 1H); 7.26 (s, 1H).

Procedure for the Synthesis of Compound 103-5 6-(Hydroxymethyl)-1-indanone

Compound 103-4 (540 mg, 2.62 mmol) was dissolved in a mixture of $H_2O$:acetone (1:4.25). pTSA (451 mg, 2.62 mmol) was added and the reaction mixture was refluxed for 1 hour. The reaction mixture was concentrated under vacuum, extracted with EtOAc, organic layer was dried over $Na_2SO_4$, filtered, and concentrated to give desired product 103-5 (423.1 mg, 99.6% yield).

m/z=207.63 $(M+H)^+$.

$^1$H NMR (300 MHZ) ($CDCl_3$) δ (ppm): 2.29 (bs, 1H); 2.67 (t, J=6.1 Hz, 2H); 3.10 (t, J=5.9 Hz, 2H); 4.72 (s, 2H); 7.44 (d, J=7.8 Hz, 1H); 7.61 (d, J=7.8 Hz, 1H); 7.70 (s, 1H).

Procedure for the Synthesis of Compound 103-6 6-{[Tert-butylbis(methyl)siloxy]methyl}-1-indanone58

Compound 103-5 (2 g, 12.33 mmol) was dissolved in DCM at 0° C. Then, added $Et_3N$ (2.1 ml, 14.72 mmol) and 4-dimethylaminopyridine (DMAP) (catalytic amount), followed by the addition of compound 2 (2.04 g, 13.6 mmol). Stirred at room temperature until complete disappearance of starting material. (1:4.25). The crude was extracted with DCM, organic layer was dried over $Na_2SO_4$, filtered, and concentrated. The crude was purified by column chromatography using Hex:EtOAc as eluent to give desired product 103-6 (1.7 g, 99.8% yield).

m/z=277.66 $(M+H)^+$.

$^1$H NMR (300 MHz) ($CDCl_3$) δ (ppm): 0.15 (s, 6H); 0.99 (s, 9H); 2.75 (t, J=5.9 Hz, 2H); 3.17 (t, J=6.2 Hz, 2H); 4.82 (s, 2H); 7.49 (d, J=7.6 Hz, 1H); 7.64 (d, J=8.2 Hz, 1H); 7.74 (s, 1H).

Procedure for the Synthesis of Compound 103-7 Ethyl (E)-(6-{[Tert-butylbis(methyl)siloxy]methyl}-1-indanylidene)acetate Triethyl phosphonoacetate (1.65 g, 7.4 mmol) was added dropwise to the suspension of NaH (295.2 mg, 12.3 mmol) in dry THF at 0° C. The reaction mixture was stirred for 1 h, under Ar atm. A solution of compound 103-6 (1.7 g, 6.15 mmol) in dry THF (5 ml) was added dropwise to the reaction mixture. The suspension was stirred at room temperature for overnight. The reaction mixture was quenched with sat.

$NH_4Cl$ solution and extracted with EtOAc. Organic layer was dried over $Na_2SO_4$, filtered, and concentrated. The crude was purified by column chromatography using Hex: EtOAc as eluent to give desired product 103-7 E-isomer (353 mg, 16.5% yield); Z-isomer (110 mg, 5.1% yield).

m/z=347.51 $[M+H]^+$.

$^1$H NMR (300 MHZ) ($CDCl_3$) δ (ppm): 0.06 (s, 6H); 0.89 (s, 9H); 1.28 (t, J=7.3 Hz, 3H); 2.96-3.03 (m, 2H); 3.22-3.29 (m, 2H); 4.18 (q, J=7.2 Hz, 2H); 4.68 (s, 2H); 6.24 (t, J=2.6 Hz, 1H); 7.26 (bs, 2H); 7.51 (bs, 1H).

Procedure for the Synthesis of Compound 103-8 (E)-2-(6-{[Tert-butylbis(methyl)siloxy]methyl}-1-indanylidene)ethanol To a solution of compound 103-7 (85 mg, 0.24 mmol) in dry toluene (1 mL) under nitrogen atmosphere, a solution of 1.0 M diisobutylaluminium hydride (DIBAL-H) (0.47 mL, 2 eq.) was added at −78° C. and the mixture stirred for 1 h. Then, a saturated $NH_4Cl$ aqueous solution was added, and the mixture was extracted with EtOAc. Organic phase was separated, dried over $Na_2SO_4$, filtered and concentrated under vacuum to afford the pure alcohol 103-8 (60 mg, 80.4% yield).

m/z=327.47 $[M+H]^+$.

$^1$H NMR (300 MHZ) ($CDCl_3$) δ (ppm): 0.16 (s, 6H); 1.00 (s, 9H); 1.63 (bs, 1H); 2.80-2.92 (m, 2H); 2.97-3.13 (m, 2H); 4.40 (d, J=7.1 Hz, 2H); 4.78 (s, 2H); 6.12-6.23 (m, 1H); 7.22-7.28 (m, 2H); 7.51 (bs, 1H).

Procedure for the Synthesis of Compound 103-9 (E)-(6-{[Tert-butylbis(methyl)siloxy]methyl}-1-indanylidene) acetaldehyde59

A solution of alcohol 103-8 (60 mg, 0.197 mmol) and $MnO_2$ (171.3 mg, 1.97 mmol) in $CH_2Cl_2$ was stirred at room temperature for 3-4 h. The unreacted $MnO_2$ was filtered off and the filtrate was washed with DCM 2-3 times. The solvent was evaporated under vacuum to give the pure aldehyde 103-9 (33 mg, 55.9% yield).

m/z=303.66 $[M+H]^+$.

$^1$H NMR (300 MHZ) ($CDCl_3$) δ (ppm): 0.11 (s, 6H); 0.95 (s, 9H); 3.03-3.14 (m, 2H); 3.27-3.40 (m, 2H); 4.75 (d, J=5.6 Hz, 2H); 6.45-6.53 (m, 1H); 7.30-7.38 (m, 2H); 7.55 (bs, 1H).

Procedure for the Synthesis of Compound 103-10 {[(E)-3-[2-(1-Azetidinyl)ethylidene]-5-indanyl]methoxy}-tert-butylbis(methyl)silane To the solution of compound 103-9 (159 mg, 0.53 mmol) was added $Ti(OiPr)_4$ (0.24 ml, 0.79 mmol). The reaction mixture was stirred at room temperature for 1 h. Then, added azetidine (33 mg, 0.58 mmol) and the reaction was stirred at rt for overnight. EtOH (2 ml) and $Na(OAc)_3BH$ (224.7 mg, 1.06 mmol) were added to the reaction mixture and was stirred at room temperature for 2-3 hours. The crude was extracted with EtOAc, organic layer was dried over $Na_2SO_4$, filtered and concentrated. The crude was purified by semi-prep HPLC to give the desired product 103-10 (yellow oil, 10 mg, 5.5% yield).

m/z=344.7 $[M+H]^+$.

$^1$H NMR (300 MHZ) (MeOD) δ (ppm): 0.01 (s, 6H); 0.83 (s, 9H); 2.12-2.28 (m, 2H); 2.65-2.79 (m, 2H); 2.84-3.00 (m, 2H); 3.46 (d, J=7.9 Hz, 2H); 3.58 (t, J=7.9 Hz, 4H); 4.49 (s, 2H); 5.70-5.82 (m, 1H); 7.08-7.18 (m, 2H); 7.38 (bs, 1H).

Procedure for the Synthesis of Compound 103 {(E)-3-[2-(1-Azetidinyl)ethylidene]-5-indanyl}methanol Compound 103-10 (10 mg, 0.029 mmol) was taken in RBF dissolved in dioxane at 0° C. the added 4 M HCl (0.014 ml, 2 eq). The reaction mixture was stirred at room temperature for 2-3 hours until complete disappearance of starting material. Solvent was evaporated to give the desired product 103 (yellow oil, 2 mg, 33.3% yield).

m/z=280.8 $[M+H]^+$.

$^1H$ NMR (300 MHZ) (MeOD) δ (ppm): 2.79 (t, J=7.6 Hz, 2H); 3.43-3.52 (m, 4H); 3.53-3.65 (m, 4H); 3.96-4.16 (m, 4H); 4.57 (s, 2H); 6.30-6.37 (m, 1H); 7.12 (d, J=7.2 Hz, 1H); 7.30-7.37 (m, 2H).

Methods

Example 16: Percent (α-Me-5-HT) Activity at 5-HT2A Assay

Compounds were tested in the IPOne HTRF (Homogeneous Time Resolved Fluorescence) assay at Epics Therapeutics S.A. (Belgium). Briefly, CHO-K1 cells expressing human recombinant 5-HT2A receptor grown to mid-log phase in culture media without antibiotics were detached with PBS-EDTA, centrifuged and resuspended in medium without antibiotics buffer. 20,000 cells were distributed in a 96 well plate and incubated overnight at 37° C. with 5% $CO_2$. For agonist testing (384-well, suspension), 5 μl of cells were dispensed on 5 μl of test compound or reference agonist in each well and the plate was incubated for 60 min. at 37° C. with 5% $CO_2$. IP1-D2 reagent and anti-IP1 cryptate reagents were then dispensed in the wells and IP1 concentrations were then measured following the manufacturer recommendations. Percent (of 5-HT) activity at 5-HT2A for compounds tested in this assay are shown in Table 2.

TABLE 3

| Compound No. | Structure | Percent (a-Me-5-HT) Activity at 5-HT2A (30 uM/0.3 μM) |
|---|---|---|
| 5 | 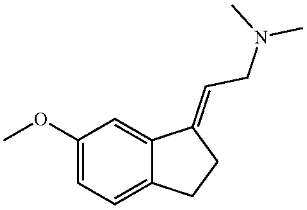 | 96/74 |
| 10 | 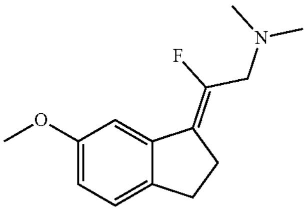 | 1/4 |

TABLE 3-continued

| Compound No. | Structure | Percent (a-Me-5-HT) Activity at 5-HT2A (30 uM/0.3 μM) |
|---|---|---|
| 12 | 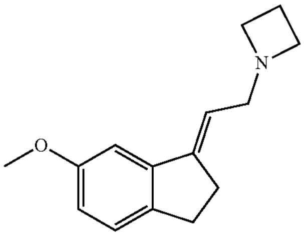 [SMILES: COc1ccc2c(c1)/C(=C/CN1CCC1)CC2] | 47/27 |
| 14 | 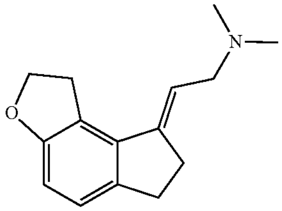 [SMILES: CN(C)C/C=C1\CCc2ccc3c(c21)CCO3] | 33/6 |
| 22 | 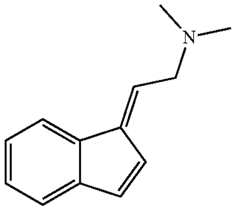 | 49/5 |
| 23 | 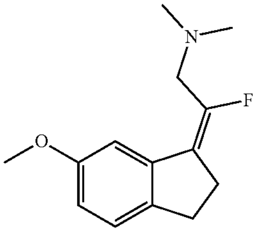 [SMILES: COc1ccc2c(c1)/C(=C(/F)CN(C)C)CC2] | −2/−1 |
| 24 | 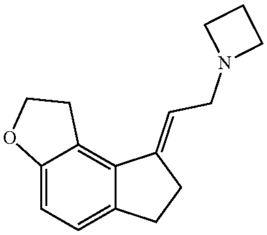 [SMILES: C(/CN1CCC1)=C1/CCc2ccc3c(c21)CCO3] | 38/17 |
| 25 | 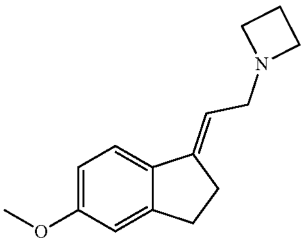 [SMILES: COc1ccc2c(c1)CC/C2=C\CN1CCC1] | −3/0 |

TABLE 3-continued

| Compound No. | Structure | Percent (a-Me-5-HT) Activity at 5-HT2A (30 uM/0.3 μM) |
|---|---|---|
| 26 | 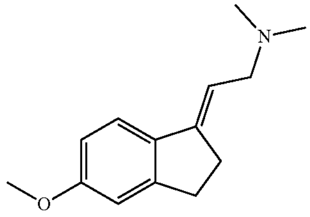 | −1/10 |
| 27 | 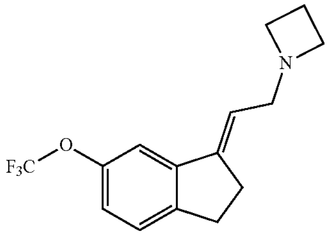 [SMILES: FC(F)(F)Oc1ccc2c(c1)/C(=C/CN1CCC1)CC2] | 8/5 |
| 28 | 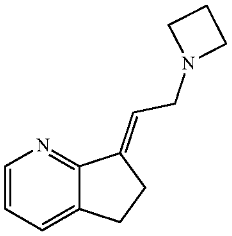 [SMILES: C(/CN1CCC1)=C1/CCc2cccnc21] | 5/5 |
| 29 | 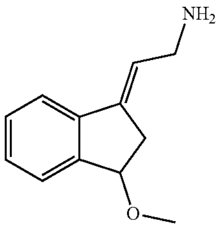 | 53/6 |
| 30 | 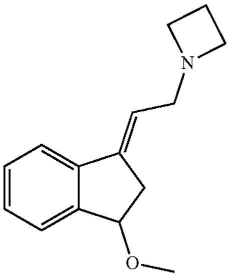 [SMILES: COC1C/C(=C\CN2CCC2)c2ccccc21] | 24/3 |
| 31 | 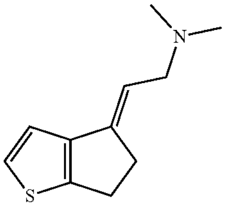 | 2/3 |

TABLE 3-continued

| Compound No. | Structure | Percent (a-Me-5-HT) Activity at 5-HT2A (30 uM/0.3 μM) |
|---|---|---|
| 101 | 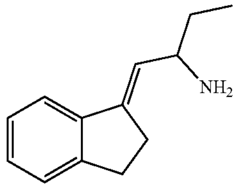 | 20/15 |
| 103 | 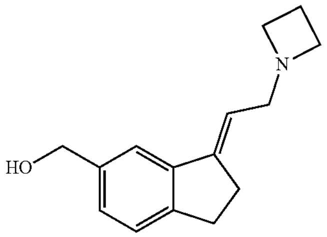 [SMILES: OCc1ccc2c(c1)/C(=C/CN1CCC1)CC2] | 94/9 |

What is claimed is:

1. A compound of Formula (Ib):

(Ib)

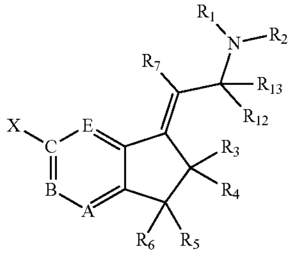

wherein:

$R_1$ is hydrogen, deuterium, or $C_1$-$C_6$ alkyl; or $R_1$ and $R_2$ can be taken together to form a 3-7 membered ring;

$R_2$ is hydrogen, deuterium, $C_1$-$C_6$ alkyl, or $C_3$-$C_6$ cycloalkyl, wherein said $C_1$-$C_6$ alkyl is optionally substituted with $C_5$-$C_6$ aryl, wherein said aryl is optionally substituted with —OH; or $R_2$ is taken together with $R_1$ to form a 3-7 membered ring;

$R_3$, $R_4$, and $R_5$ are independently hydrogen, deuterium, halogen, —$OR_{11}$, —$CF_3$, $C_1$-$C_6$ alkyl, or $C_1$-$C_6$ heteroalkyl;

$R_6$ is hydrogen or deuterium;

A is nitrogen or —C(H)—;

B is nitrogen, —C(H)—, or —C($OR_8$)—;

E is —C(H)—, —C(OH)—, —C($OR_8$)—; or

A or E is optionally sulfur while B is omitted resulting in a 5 membered thiophene ring;

C is carbon or nitrogen;

$R_7$ is hydrogen, deuterium, or $C_1$-$C_6$ alkyl;

$R_8$ is $C_1$-$C_6$ alkyl;

X is hydrogen, deuterium, halogen, —OH, —$OR_{11}$, —$SO_2NHR_{11}$, —$SO_2N(R_{11})_2$, —$SO_2R_{11}$, —$NH_2$, —$NR_{11}$, —CN, —$COOR_{11}$, —$COR_{11}$, —$CONR_{11}$, —$NCOR_{11}$, $C_1$-$C_6$ alkyl, or $C_1$-$C_6$ heteroalkyl, wherein said $C_1$-$C_6$ alkyl, or $C_1$-$C_6$ heteroalkyl is optionally substituted with $C_3$-$C_6$ cycloalkyl, or X is absent; or X and E can optionally be taken together to form a 4-7 membered substituted or unsubstituted ring wherein X is not nitrogen; or X and E can be taken together to form a 5-6 membered cycloalkyl or a 5-6 membered heterocyclyl;

$R_{11}$ is $C_1$-$C_6$ alkyl, —$CF_3$, $C_5$-$C_6$ heteroaryl, or $C_5$-$C_6$ aryl;

$R_{12}$ is hydrogen, deuterium, $C_1$-$C_6$ alkyl, —OH, or —$OR_8$; or $R_{12}$ can be taken together with $R_1$ to form a 4-7 membered saturated ring; and $R_{13}$ is hydrogen;

wherein $R_1$, $R_2$, and $R_{12}$ are not all hydrogen;

wherein $R_1$ and $R_2$ are not both ethyl;

wherein $R_1$ and $R_2$ do not form a pyrrolidine ring; and wherein $R_1$ and $R_{12}$ do not form an imidazoline ring;

or a pharmaceutically acceptable salt thereof.

2. The compound of claim 1, wherein $R_1$ and $R_2$ are $CH_3$.

3. The compound of claim 1, wherein X is —H, —OH, or —$OR_{11}$.

4. The compound of claim 1, wherein $R_5$ is —H.

5. The compound of claim 1, wherein $R_7$ is —H, or $CH_3$.

6. The compound of claim 1, wherein $R_3$ is —H or —$CH_3$.

7. The compound of claim 1, wherein E is —COH or —$COR_8$.

8. The compound of claim 1, wherein E is —$COCH_3$.

9. The compound of claim 1, wherein X and E form a 4-7 membered substituted or unsubstituted ring wherein X is not nitrogen.

10. The compound of claim 1, wherein C is nitrogen.

11. The compound of claim 1, wherein $R_2$ is isopropyl.

12. The compound of claim 1, wherein $R_1$ and $R_2$ form a 4-7 membered ring.

13. The compound of claim 1, wherein the compound is an agonist of a 5-HT2A receptor.

14. The compound of claim 1, wherein the compound modulates a serotonin receptor.

15. The compound of claim 1, wherein the compound is of Formula (IIIa):

Formula (IIIa)

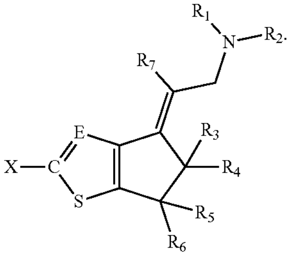

16. The compound of claim 1, wherein the compound is of Formula (IIIb):

Formula (IIIb)

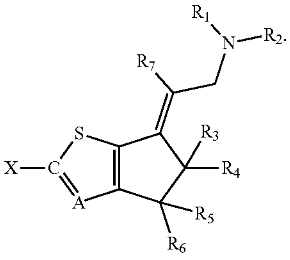

17. A compound according to claim 1, wherein the compound is selected from:

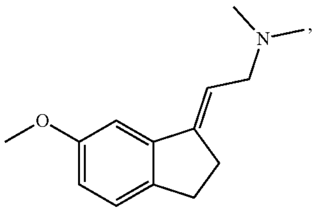

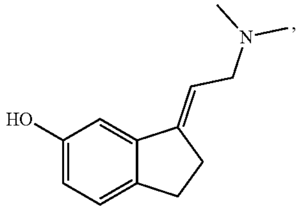

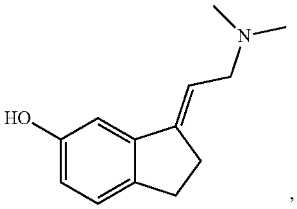
,
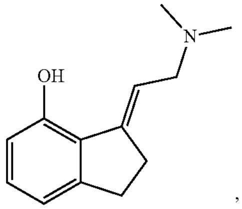
,
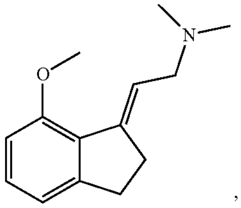
,
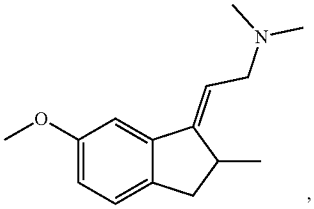
,
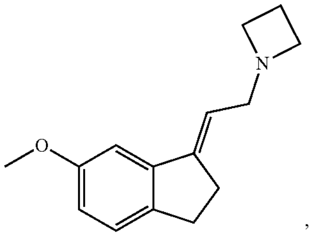
,
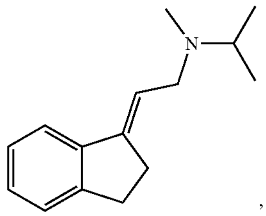
,
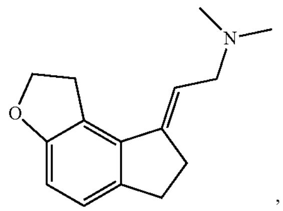
,
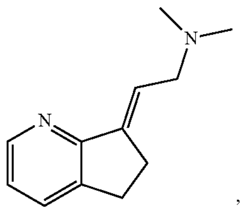
, -continued
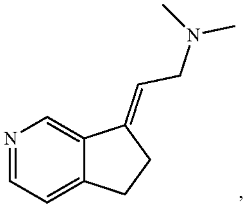
,
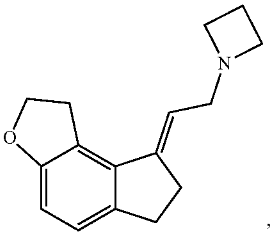
,
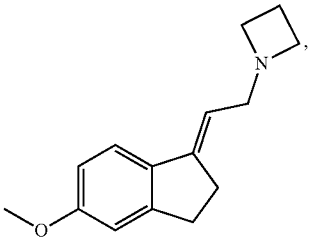
,
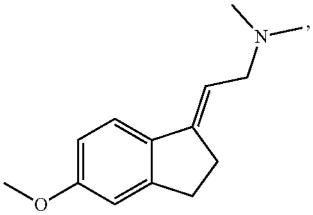
,
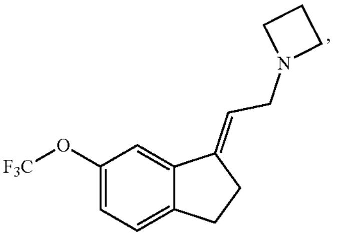
,
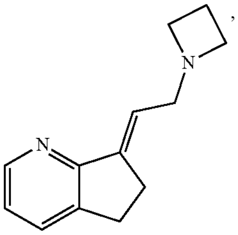
,
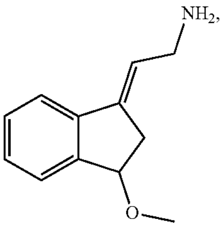
,
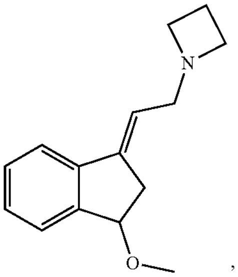
,
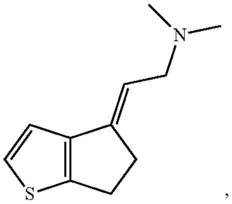
,
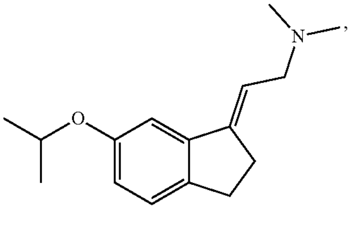
,
-continued
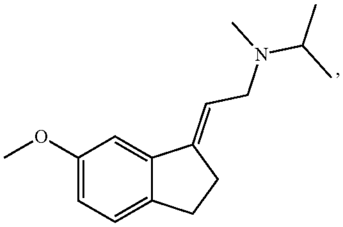
,
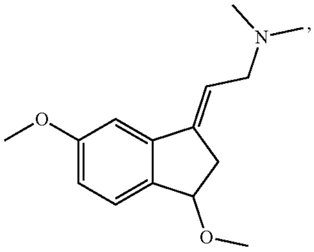
,
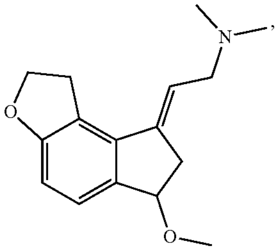
,
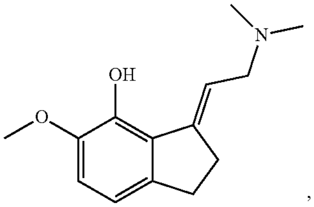
,
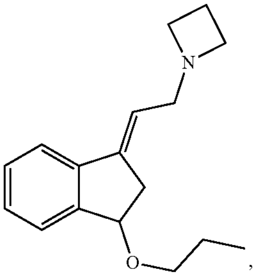
,
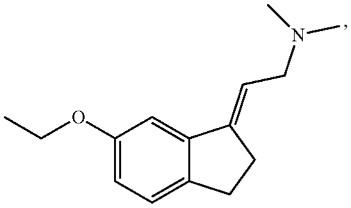
,
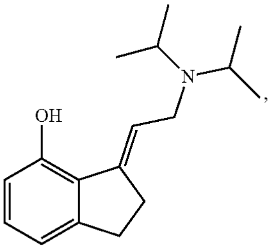
,
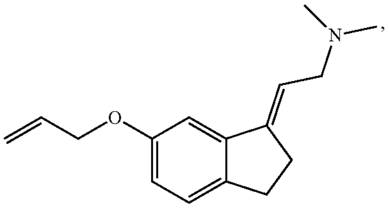
, -continued
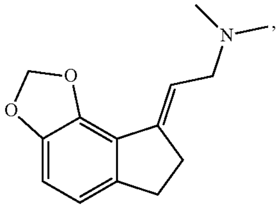,
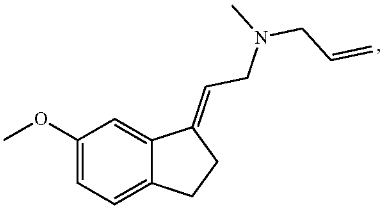,
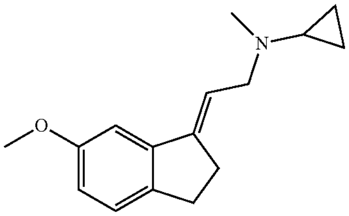,
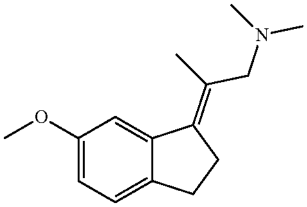, 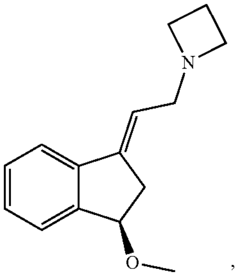,
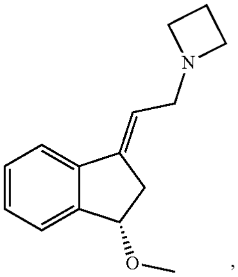, 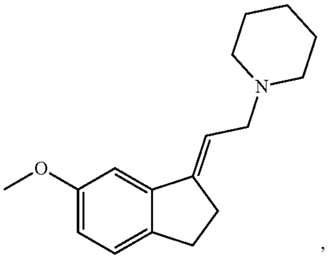,
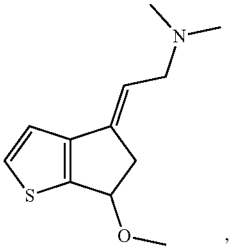, 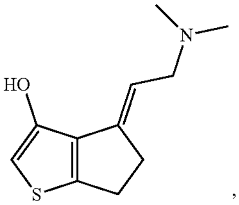,
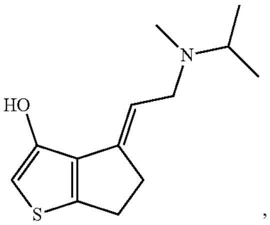, 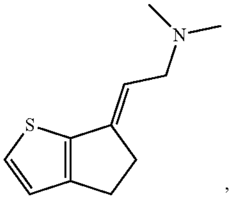,
-continued
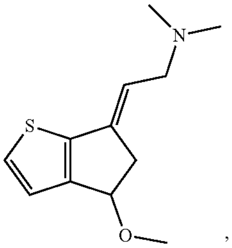, 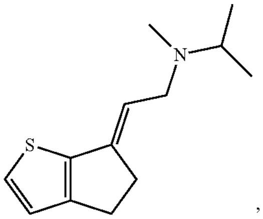,
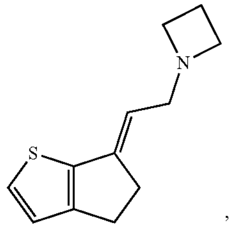, 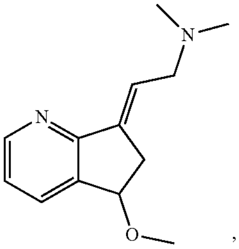,
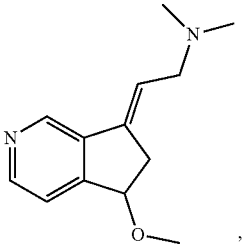, 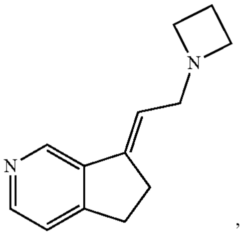,
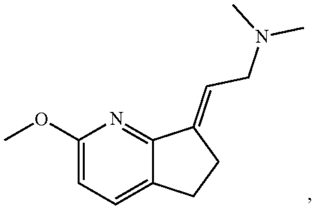, 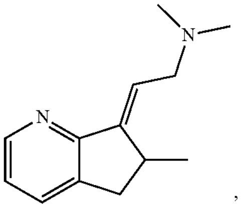,
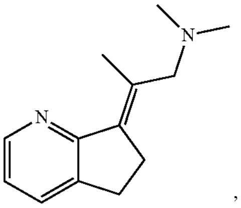, 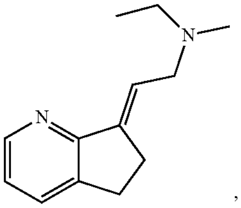,
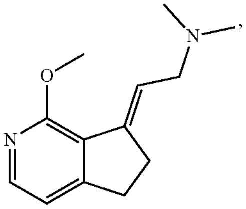,
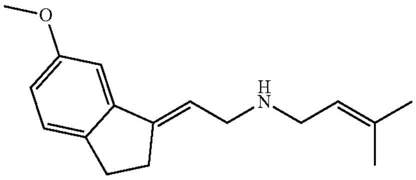, -continued
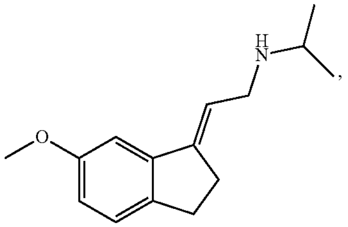
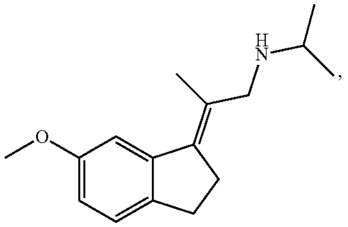
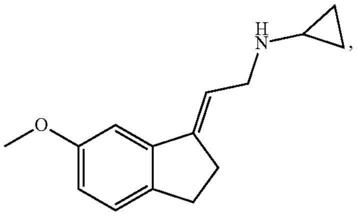
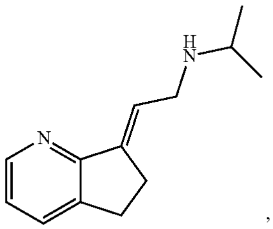
,
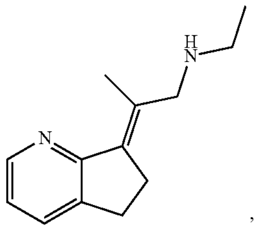
,
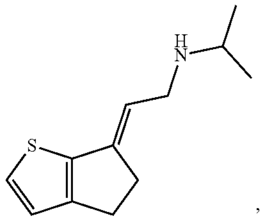
,
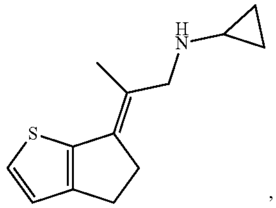
,
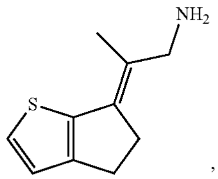
,
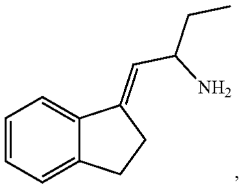
,
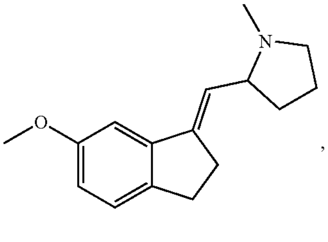
,
-continued
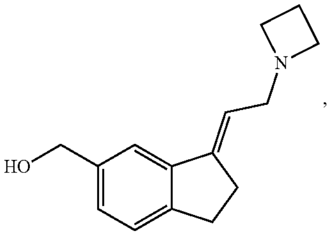
,
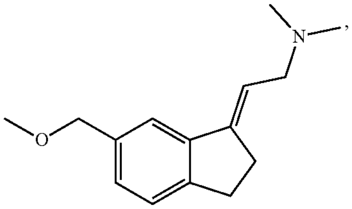
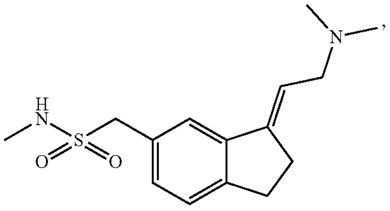
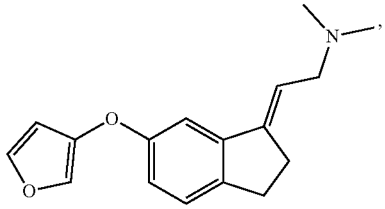
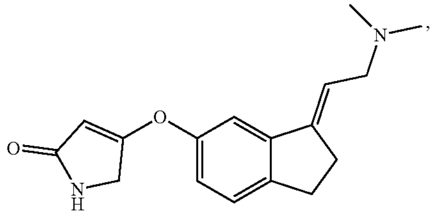
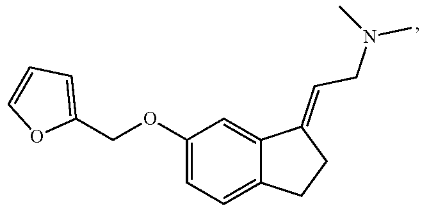
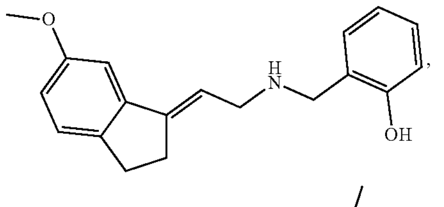
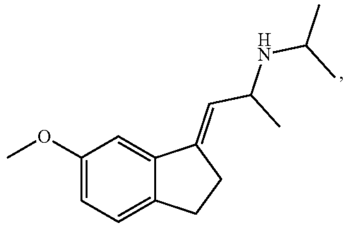

-continued
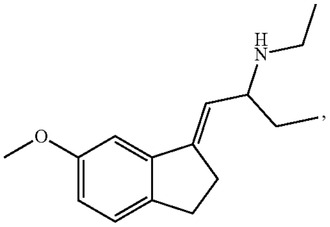
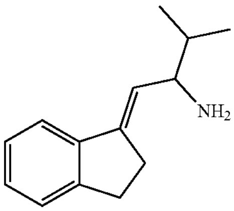
,
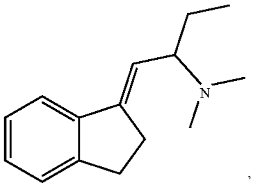
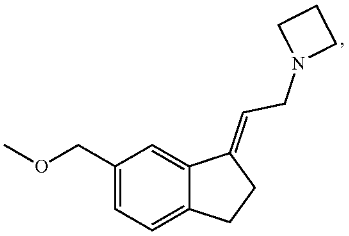
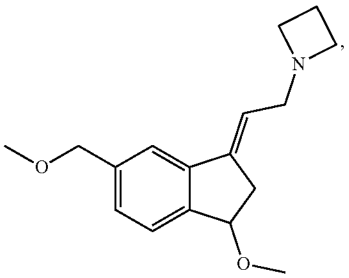
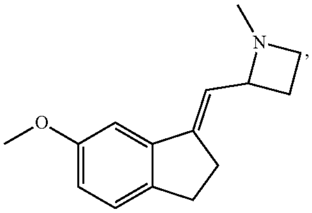
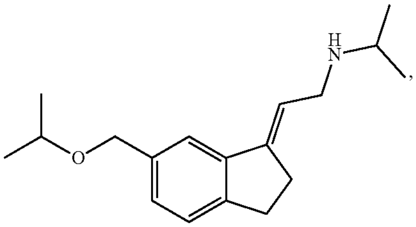
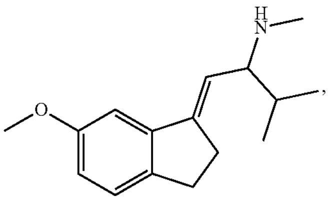
-continued
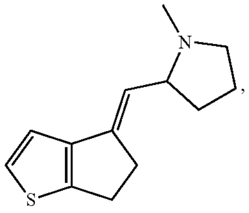
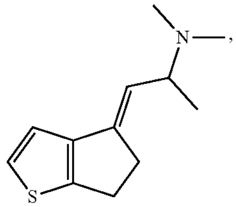
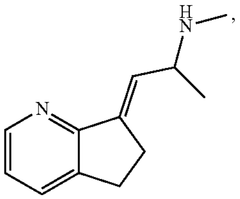
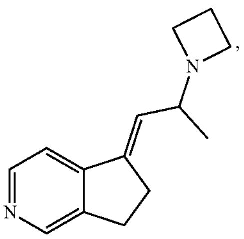
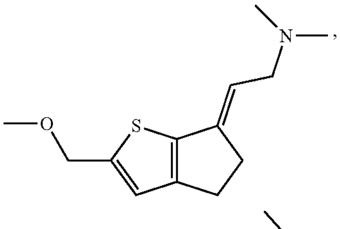
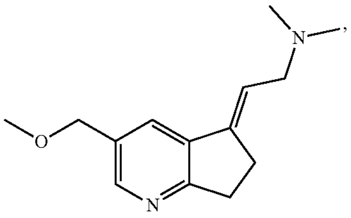
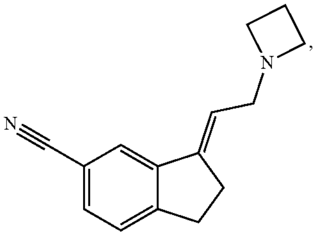
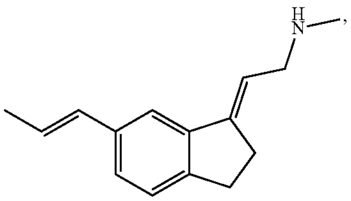

-continued
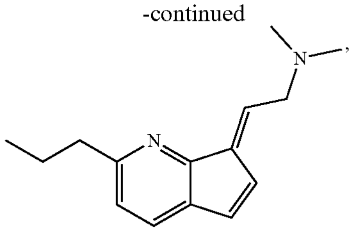
, or
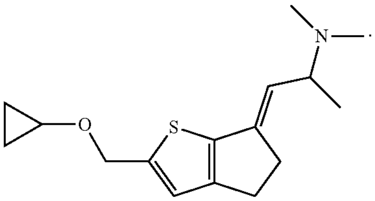
.
18. A pharmaceutical composition comprising a therapeutically effective amount of a compound of claim 1, and a pharmaceutically acceptable carrier.
19. The compound of claim 1, wherein B is nitrogen or —C(H)—; and $R_7$ is hydrogen, deuterium, or $C_1$-$C_6$ alkyl.
* * * * *